US005512442A

United States Patent [19]
Jalkanen et al.

[11] Patent Number: 5,512,442
[45] Date of Patent: Apr. 30, 1996

[54] DETECTION OF VASCULAR ADHESION PROTEIN-1 (VAP-1)

[76] Inventors: Sirpa Jalkanen, Rouvolantie 79, 20760 Piispanristi; Marko Salmi, Vähä-Hämeenkatu 12a B30, Turku, both of Finland

[21] Appl. No.: 447,800

[22] Filed: May 23, 1995

Related U.S. Application Data

[60] Division of Ser. No. 306,483, Sep. 15, 1994, which is a continuation-in-part of Ser. No. 124,490, Sep. 21, 1993, abandoned, which is a continuation-in-part of Ser. No. 895,354, Jun. 9, 1992, abandoned.

[51] Int. Cl.$^6$ .................................................. G01N 33/53
[52] U.S. Cl. ............................ 435/7.21; 435/7.2; 435/7.1
[58] Field of Search ........................... 435/7.1, 7.2, 7.21, 435/7.24; 530/388.22

[56] References Cited

FOREIGN PATENT DOCUMENTS 0289949  4/1982  European Pat. Off. .

OTHER PUBLICATIONS

Airas et al., "Lymphocyte–Vascular Adhesion Protein–2 Is a Novel 70–kDa Molecule Involved in Lymphocyte Adhesion to Vascular Endothelium," *J. Immunol.* 151(8):4228–4238 Oct. (1993).
Balass et al., "Identification of a hexapeptide that mimics a conformation–dependent binding site of acetylcholine receptor by use of a phage–epitope library," *PNAS USA* 90:10638–10642 Nov. (1993).
Berg et al., "The Human Peripheral Lymph Node Vascular Addressin is a Ligand for LECAM–1, the Peripheral Lymph Node Homing Receptor," *J. Cell Biol.* 114(2):343–349 Jul. (1991).
Bevilacqua et al., "Identification of an inducible endothelial–leukocyte adhesion molecule," *PNAS USA* 84:9238–9242 Dec. (1987).
Butcher E. C., "Leukocyte–Endothelial Cell Recognition: Three (or More) Steps to Specificity and Diversity," *Cell* 67:1033–1036 Dec. (1991).
Cotran et al., "Induction and Detection of a Human Endothelial Activation Antigen In Vivo," *J. Exp. Med.* 164:661–666 Aug. (1986).
de Fougerolles et al., "Characterization of ICAM–2 and Evidence for a Third Counter–Receptor for LFA–1," *J. Exp. Med.* 174:253–267 Jul. (1991).
Freeman et al., "An ancient, highly conserved family of cysteine–rich protein domains revealed by cloning type I and type II murine macrophage scavenger receptors," *PNAS USA* 87:8810–8814 Nov. (1990).
Friedman et al., "Cloning and characterization of cyclophilin C–associated protein: A candidate natural cellular ligand for cyclophilin C," *PNAS USA* 90:6815–6819 Jul. (1993).
Geoffroy et al., "Evidence for a Distinct Lymphocyte Homing Specificity Involved in Lymphocyte Migration to Lung–Associated Lymph Nodes," *FASEB J.* 2:A667, Abstract No. 2152 (1988).
Harris and Emery, "Therapeutic Antibodies—the coming of age," *TiBTECH* 11:42–46 Feb. (1993).
Hattori et al., "Stimulated Secretion of Endothelial von Willebrand Factor is Accompanied by Rapid Redistribution to the Cell Surface of the Intracellular Granule Membrane Protein GMP–140," *J. Biol. Chem.* 264(14):7768–7771 May (1989).
Jalkanen et al., "A Distinct Endothelial Cell Recognition System that Controls Lymphocyte Traffic into Inflamed Synovium," *Science* 233:556–558 Aug. (1986).
Jalkanen et al., "In Vitro Analysis of the Homing Properties of Human Lymphocytes: Developmental Regulation of Functional Receptors for High Endothelial Venules," *Blood* 66(3):577–582 Sep. (1985).
Jalkanen et al., "A Novel Endothelial Cell Antigen Involved in Lymphocyte Binding to High Endothelial Venules," *Keystone Symp. Mol. Cell. Biol., Suppl. 16 F*, p. 107, Abstract No. W610 (Apr. 3–16, 1992).
Osborn et al., "Direct Expression Cloning of Vascular Cell Adhesion Molecule 1, A Cytokine–Induced Endothelial Protein that Binds to Lymphocytes," *Cell* 59:1203–1211 Dec. (1989).
Osborn, L., "Leukocyte Adhesion to Endothelium in Inflammation," *Cell* 62:3–6 Jul. (1990).
Rice et al., "Vascular and Nonvascular Expression of INCAM–110, A Target for Mononuclear Leukocyte Adhesion in Normal and Inflamed Human Tissues," *Amer. J. Pathol.* 138(2):385–393 Feb. (1991).
Rosen et al., "Involvement of Sialic Acid on Endothelial Cells in Organ–Specific Lymphocyte Recirculation," *Science* 228:1005–1007 May (1985).
Salmi and Jalkanen, "A 90–Kilodalton Endothelial Cell Molecule Mediating Lymphocyte Binding in Humans," *Science* 257:1407–1409 Sep. (1992).
Salmi et al., "A Novel Endothelial Cell Antigen Involved in Lymphocyte Binding to High Endothelial Venules," *Eur. Feb. Immunol. Soc.*, 11th Meeting Abstracts, Abstract No. 21–12 (Jun. 9, 1991).
Salmi et al., "Induction and Function of Vascular Adhesion Protein–1 at Sites of Inflammation," *J. Exp. Med.* 178:2255–2260 Dec. (1993).
Stoolman, L. M. "Adhesion Molecules Controlling Lymphocyte Migration," *Cell* 56:907–910 Mar. (1989).
Wellicome et al., "A Monoclonal Antibody that Detects A Novel Antigen on Endothelial Cells that is Induced by Tumor Necrosis Factor, IL–1, or Lipopolysaccharide," *J. Immunol.* 144(7):2558–2565 Apr. (1990).

*Primary Examiner*—Christina Y. Chan
*Assistant Examiner*—Phillip Gambel
*Attorney, Agent, or Firm*—Sterne, Kessler, Goldstein & Fox

[57] ABSTRACT

A novel endothelial cell molecule, VAP-1, is described that mediates lymphocyte binding in man. Further described are anti-VAP-1 monoclonal antibodies and methods for the diagnosis and treatment of inflammatory and autoimmune diseases by the administration of VAP-1 binding compounds, such as anti-VAP-1 antibodies.

21 Claims, 22 Drawing Sheets

T E D G D M X |L V N G A S A N E G| X V E

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

Leu Val Asn Gly Ala Ser Ala Asn Glu Gly
1               5                   10

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:2:

Thr Glu Asp Gly Asp Met Xaa Leu Val Asn Gly Ala Ser Ala Asn Glu
1               5                   10                  15

Gly Xaa Val Glu
            20

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:3:

CTTGGATCCA GGCAATGGCT CTCCTGT                                           27

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:4:

CCCCTCGAGT TACACCATGT CAGTGGAGT                                         29

DETECTION OF VASCULAR ADHESION PROTEIN-1 (VAP-1)

This application is a divisional of application Ser. No. 08/306,483, filed Sep. 15, 1994 which is a continuation-in-part of U.S. application Ser. No. 08/124,490, filed Sep. 21, 1993 which is now abandoned, which is a continuation-in-part of U.S. application Ser. No. 07/895,354, filed Jun. 9, 1992 which is now abandoned.

FIELD OF THE INVENTION

The present invention is directed to a novel human endothelial cell adhesion antigen, designated VAP-1, monoclonal antibodies that recognize the VAP-1 antigen, and to the use of such molecules in diagnosing and treating chronic and acute inflammatory and infectious conditions characterized by lymphocyte migration.

BACKGROUND OF INVENTION

Most mature lymphocytes continuously recirculate between the blood and lymphatic organs (Butcher, E. C., *Curr. Top. Microbiol. Immunol.* 128:85 (1986)). Lymphocytes leave the blood by recognizing and binding to the vascular endothelial cells. Thereafter, they migrate between the endothelial cells into the surrounding tissues. Lymphocyte trafficking allows the full repertoire of lymphocyte specificities to be available for immune reactions throughout the body, and it also facilitates the cell-cell interactions required for the generation and control of immune responses. Lymphocyte adherence to endothelial cells is dependent on interactions between complementary adhesion molecules expressed on both cell types (Springer, T. A., *Nature* 346:425 (1990); Stoolman, L. M., *Cell* 56:907 (1989); Osborn, L., *Cell* 62:3 (1990); Pober and Cotran, *Transplantation* 50:537 (1990); Butcher, E. C., *Cell* 67:1033 (1991)). Under normal conditions, lymphocytes mainly bind to specialized postcapillary venules called high endothelial venules (HEV). Functionally separate lymphocyte-HEV recognition systems mediating lymphocyte migration to peripheral lymph nodes, mucosal lymphoid organs, synovium, skin and lung-associated lymphoid tissues in an organ-specific manner have been described (Butcher, E. C., et al., *Eur. J. Immunol.* 10:210 (1980); Jalkanen, S., et al., *Science* 233:556 (1986); Picker, L. J., et al., *Nature* 349:796 (1991); Geoffrey, J. S., et al., *FASEB J.* 2:A667 (1988)). In inflammation, activation of the endothelial cell results in changes of its adhesion molecule status, which largely determines the magnitude and type of leukocyte influx into the affected tissue. Thus, endothelial cell molecules are a key element in controlling the characteristics of local immune response, and obviously, a detailed understanding of the mechanisms regulating lymphocyte traffic and leukocyte extravasation can provide new means to clinically manipulate the inflammatory response.

Since in man the endothelial cell ligands mediating tissue-selective lymphocyte homing are largely unknown, a need exists for the identification of such molecules.

SUMMARY OF THE INVENTION

Recognizing the importance of controlling inflammation, and cognizant of the need to understand the endothelial cell ligands that mediate tissue-selective lymphocyte homing, the inventors attempted to identify such molecules as expressed by human synovial vessels. These studies have culminated in the identification of a novel endothelial cell molecule that mediates lymphocyte binding in man, VAP-1, and the production of monoclonal antibodies against the same. These antibodies are useful in assays for the quantitative and qualitative assessment of VAP-1 levels, and in clinical treatments designed to antagonize VAP-1 action in a patient in need of such treatment.

The inventors have discovered that two species of VAP-1 (90 kD and 170 kD) exist in lymphatic tissues. To elucidate the relationship between the 90 kD and 170 kD species, the inventors have purified these two forms of the VAP-1 protein. Thus, one aspect of the invention is directed to a purified VAP-1 protein which migrates at a molecular weight of about 170 kD when VAP-1 is resolved by gradient sodium dodecylsulfate polyacrylamide gel electrophoresis (5–12.5% SDS-PAGE) under non-reducing conditions and is visualized by immunoblotting with the monoclonal antibody 1B2. The inventors have further discovered that VAP-1 also migrates at a molecular weight of about 170 kD when metabolically labeled, immunoprecipitated with 1B2, and resolved by gradient SDS-PAGE (5–12.5%) under reducing conditions. However, VAP-1 migrates as a 180–200 kD protein when it is visualized either by silver staining immunopurified VAP-1 or by immunoprecipitating surface iodinated tonsil tissue and resolved by linear SDS-PAGE (7.5%) under reducing conditions.

Thus, depending on the purification technique and gel conditions, this form of VAP-1 will migrate as either an about 170-kD or an about 180–200 kD protein. However, for clarity, this form of VAP-1 will herein be referred to as the 170 kD form.

The inventors have further discovered that the 170 kD VAP-1 is the mature form of this adhesion protein and is modified with sialic acids which are indispensable for its adhesive function.

A second aspect of the invention is directed to the 90 kD form of the VAP-1 protein wherein said protein migrates at a molecular weight of about 90 kD when immunopurified or immunoprecipitated with 1B2 and resolved by linear SDS-PAGE (7.5%) or gradient SDS-PAGE (5–12.5%) under reducing conditions. The 90 kD form of VAP-1 migrates as an approximately 100 kD protein under non-reducing conditions. The inventors have discovered that the 90 kD form of VAP-1 is also modified with sialic acids and may be a proteolytic degradation product of the mature 170 kD form of VAP-1.

The invention is further directed to antibodies against VAP-1 protein, especially monoclonal antibodies, and compositions containing such antibodies. The monoclonal antibody 1B2 is provided by this invention as well as the hybridoma cell line which produces it (DSM ACC2041).

The invention is further directed to antibodies against "mimotopes" of the VAP-1 protein, especially monoclonal antibodies, and compositions containing such antibodies. Like antibodies against the VAP-1 protein itself, antibodies, especially monoclonal antibodies, against mimotopes of the VAP-1 protein are also capable of antagonizing VAP-1-mediated binding of lymphocytes to endothelial cells. The inventors have discovered that there is mimotypic identity between the N-terminus of the mouse cyclophilin C associated protein (mCyCAP) and the VAP-1 protein.

Thus, the invention is further directed to a method for antagonizing VAP-1-mediated binding of lymphocytes to endothelial cells, said method comprising inhibiting the VAP-1-mediated lymphocyte-endothelial cell adhesion reaction by providing amounts of a VAP-1 binding compound sufficient to block the VAP-1 endothelial cell sites that participate in such reaction, especially where such lymphocyte-endothelial cell adhesion reaction is associated with chronic or acute inflammatory or infectious diseases such as arthritis, rheumatoid arthritis, dermatosis, inflammatory bowel disease, autoimmune diseases, psoriasis, atopic eczema, lichen ruber planus, Crohn's disease, and ulcerative colitis. Preferred VAP-1 binding compounds are monoclonal antibodies against VAP-1 itself and monoclonal antibodies against mimotopes of VAP-1.

The invention is further directed to a method of diagnosing a medical condition that is mediated by VAP-1-mediated binding of lymphocytes to endothelial cells in a subject, said method comprising detecting anti-VAP-1 antibody binding to VAP-1 positive cells taken from such subject, and diagnosing said medical condition on the basis of such binding, such medical conditions including chronic or acute inflammatory or infectious diseases such as arthritis, rheumatoid arthritis, dermatoses, inflammatory bowel diseases, and autoimmune diseases, psoriasis, atopic eczema, lichen ruber planus, Crohn's disease, and ulcerative colitis. In an alternative embodiment, an antibody against a mimotope of VAP-1 can be substituted for the anti-VAP-1 antibody when diagnosing said medical condition.

DETAILED DESCRIPTION OF THE INVENTION

Figure 1A:
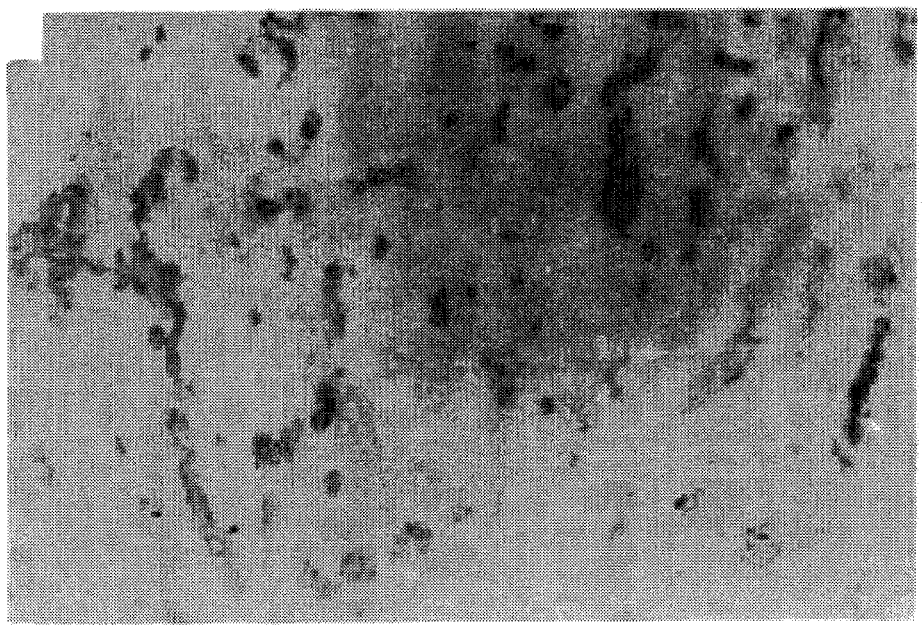
FIG. 1 (A–D). Distribution of VAP-1 in human tissues. (A) In inflamed synovial membrane, mAb 1B2 strongly stains HEV-like vessels. (B) In tonsil, expression of VAP-1 in HEV varies from intense (arrowheads) to very weak (arrows) or negative. (C) Immunofluorescence staining of a tonsil shows the prominent expression of VAP-1 on the luminal surface of the vessels (arrows). (D) In appendix, only few weakly staining HEV are seen (arrowheads). Magnifications: A is×100; B is×250; C and D are×400.

Interactions between leukocyte surface receptors and their ligands on vascular endothelial cells critically control lymphocyte traffic between the blood and various lymphoid organs, as well as extravasation of leukocytes into sites of inflammation. We describe here a novel human endothelial cell adhesion molecule (VAP-1) defined by a monoclonal antibody 1B2. A hybridoma cell line producing monoclonal antibody 1B2 was deposited under the terms of the Budapest Treaty with the International Depository Authority DSM Deutsche Sammlung Von Mikroorganismen Und Zellkulturen GmbH at the address Mascheroder Weg 1 B, D-3300 Braunschweig, GERMANY. The deposit was made on Jun. 9, 1992, and given the accession number DSM ACC2041. Two species of VAP-1 (170 kD and 90 kD) exist in lymphatic tissues. The about 170 kD VAP-1 is the mature form of this adhesion molecule. VAP-1 is preferentially expressed on synovial, peripheral lymph node and tonsil high endothelial venules (HEV) and 1B2 markedly inhibits lymphocyte binding to HEV in these tissues, as opposed to those at mucosal sites. Moreover, lymphocytes bind to immunoaffinity-isolated VAP-1 in an 1B2-inhibitable manner. The expression pattern, molecular weight, and functional properties define VAP-1 as a new endothelial ligand for lymphocytes. In lymphatic tissue, VAP-1 is modified with sialic acids that are crucial for its adhesive function.

VAP-1 is absent from the surface of cultured endothelial cells (human umbilical vein endogherial cells, HUVEC, and an endothelial cell hybrid, HEC). However, when studied for intracellular expression of VAP-1, HUVEC and HEC display definitive staining with 1B2. Thus, in HEC and HUVEC, VAP-1 is present in the cytoplasm and not on the cell surface, whereas in tonsil HEV, VAP-1 is both lumenal and in discrete cytoplasmic granules. Moreover, in HEC, VAP-1 is not posttranslationally modified with sialic acids. The lack of surface expression of VAP-1 in HEC may be due to the defective sialylation of VAP-1 in these cells. The distinct oligosaccharide modifications of VAP-1 in the cultured endothelial cells as compared to the in vivo situation underscores the potential risks of using cell lines as the sole model for studying the function of endothelial adhesion molecules.

We conclude that VAP-1 is a novel endothelial sialoglycoprotein that mediates lymphocyte binding to vessels. Both sialic acid and conformation-dependent protein residues of VAP-1 are required to produce the functional binding site to interact with its counterreceptors on leukocytes.

Production of Antibodies

For the initial identification of VAP-1 protein, monoclonal antibodies against synovial vessels were produced by immunizing an appropriate animal, such as mice, with stromal elements of human synovium. Such stromal elements of human synovium may be obtained using methods known in the art. Synovial stroma may be isolated by depleting the lymphocytes from the synovial tissue. The synovial tissue is minced and the minced tissue pressed through a stainless steel screen. The stromal elements are collected from the top of the screen.

The immunogen is preferably administered together with an adjuvant, such as, for example, incomplete Freund's adjuvant; however, any appropriate adjuvant may be used. The immunogen and adjuvant are injected by any regime or protocol that will result in the induction of antibodies synthesis. For example, injection of the immunogen (synovial stromal elements containing approximately 1 µg VAP-1 antigen per injection) three times, at one week intervals, into the footpads of specific-pathogen free Balb/c mice, will induce the immune response.

Lymphocytes from popliteal lymph nodes are isolated using methods known in the art as described above, by pressing the minced lymph nodes through a stainless steel screen and collecting the released lymphocytes from the flow though, and fused with the nonsecreting NS-1 mouse myeloma cells (available from the ATCC, No. TIB 18) using standard protocols. Hybridomas may be screened using any appropriate method, such as immunoperoxidase staining of frozen sections. One hybridoma (1B2, subclass IgG$_1$) that produced an antibody reactive with vascular endothelium of synovium, was cloned twice by limiting dilution and was chosen for further analysis. The antigen recognized by mAb 1B2 was named VAP-1 (for Vascular Adhesion Protein-1). A second monoclonal antibody, mAb 3B11, was raised against the 170 kD form of VAP-1 as described above. Thus, in addition to synovial stroma, purified VAP-1 can also be used as an immunogen for raising anti-VAP-1 monoclonal antibodies. Like 1B2, mAb 3B11 specifically recognizes VAP-1 and can thus be used for purification and detection of this protein.

Antibodies used in the methods of the invention as VAP-1 binding compounds are preferably antibodies with a specificity against VAP-1, or an antigenic fragment thereof. Such antibodies may be both polyclonal and monoclonal.

Antibodies with specificity for VAP-1 include monoclonal antibodies against VAP-1 itself as described above and monoclonal antibodies against mimotopes of VAP-1. Mimotopes are defined as conformationally, but not linearly, related structures that react with a given antibody. In other words, mimotopes are cross-reacting epitopes which are conformationally related due to similarities in three dimensional folding rather than amino-acid sequence. For example, a functional anti-acetylcholine receptor monoclonal antibody specifically recognizes a certain hexamer sequence from peptide display phage library, although the hexamer sequence does not exist in the acetylcholine receptor (Balass et al., *PNAS USA* 90:10638 (1993)).

By the invention, VAP-1-specific monoclonal antibodies can also be raised by immunizing appropriate animals, such as mice, with mimotopes of VAP-1. The inventors have discovered that there is mimotypic identity between the N-terminus of the mouse cyclophilin C associated protein (mCyCAP) and the VAP-1 protein. In particular, VAP-1-specific antibodies can be raised by immunizing mice with amino acids 8–17 of the N-terminus of mCyCAP according to the methodology described above and in the examples. Briefly, approximately 50 µg of purified decamer peptide (LVNGASANEG) [SEQ. ID. NO. 1] from the N-terminus of mCyCAP in incomplete Freund's adjuvant is injected into footpads of specific pathogen free Balb/C mice three times at one week's intervals. Lymphocytes from popliteal lymph nodes are isolated as described above. These are then fused with nonsecreting NS-1 mouse myeloma cells using standard protocols. Hybridomas may be screened using any appropriate method, including immunostaining in tonsil, in peptide EIA, and in dot blot assays. Using this method, the inventors have discovered a monoclonal antibody (5B11) which reacts with the same cell types as 1B2 in tonsil. Moreover, 5B11 specifically recognizes the 170 kD from of VAP-1, but not the 90 kD form, in immunoblotting of tonsil lysates. A hybridoma cell line producing monoclonal antibody 5B11 was deposited under the terms of the Budapest Treaty with the International Depository Authority DSM-Deutsche Sammlung von Mikrrorganismen Und Zellkulturen GmbH at the address Mascheroder Weg 1b, D-38124 Braunschweig, GERMANY. The deposit was received by the International Depository Authority on Sep. 29, 1995 and given the accession number DSM ACC2237.

It should be recognized that the N-terminus of mCyCAP is but one mimotope of VAP-1 that can be used to raise VAP-1-specific monoclonal antibodies that are capable of antagonizing VAP-1-mediated binding of lymphocytes to endothelial cells. The mCyCAP protein belongs to a superfamily of proteins containing a scavenger receptor cysteine rich (SRCR) domain. Since 5B11, which blocks lymphocyte binding to vessels, was raised against the SRCR-like domain of mCyCAP, any protein in the superfamily of proteins containing a SRCR-like domain is a possible mimotope of VAP-1. The superfamily of proteins containing an SRCR-like domain is described in Freeman et al., *PNAS (USA)* 87:8810 (1990). Using the methods set forth above and in the examples, the skilled artisan could readily screen any particular candidate polypeptide having an SRCR-like domain to determine if it is capable of raising a VAP-1-specific monoclonal antibody that antagonizes VAP-1-mediated binding of lymphocytes to endothelial cells.

Polyclonal antibodies may be prepared by injecting a suitable animal with a substantially pure preparation of VAP-1 or a mimotope of VAP-1 followed by one or more booster injections at suitable intervals.

It is, however, preferred to employ monoclonal antibodies (or biologically active derivatives thereof such as Fab', $F(ab')_2$ or Fv fragments), directed against VAP-1 antigen or against a VAP-1 mimotope antigen, in the methods of the invention. It should be noted that the monoclonal antibodies may be from any suitable source, and may thus be selected from, for instance, murine or human monoclonal antibodies.

The antibody may also be produced by cloning a DNA sequence coding for the antibody or a biologically active derivative thereof into suitable cell, e.g., a microbial, plant, animal or human cell, and culturing the cell under conditions conducive to the production of the antibody or biologically active derivative in question and recovering the antibody or biologically active derivative thereof from the culture.

The antibodies used in the reagent of the invention should preferably be in substantially pure form in order to improve the accuracy of the method.

Characteristics of VAP-1

To isolate VAP-1 antigen, a lymphocyte-depleted tonsilar extract is the preferred source of the VAP-1 protein. These extracts are prepared by depleting the lymphocytes from tonsilar tissue by pressing the minced tissue through a stainless steel screen. The stromal elements are collected from the top of the screen. However, any cell type that expresses VAP-1 may be used in the procedure below as the exemplified procedure relies on the affinity of VAP-1 for 1B2 mAb for the final isolation.

All steps should be performed at refrigerated temperatures (about 4° C.). The cells are gently lysed (for example overnight at 4° C.) in an buffer that contains agents for the inhibition of proteolysis, such as a buffer containing 150 mM NaCl, 10 mM Tris-base, 1.5 mM $MgCl_2$, 1% NP40, 1 mM PMSF and 1% aprotinin. Such extracts are preferably then cleared of cell lysis debris by a mild centrifugation at, for example, 10,000 g for 30 min. The supernatant is then applied to a series of affinity columns that provide as the affinity agent, in succession, (1) normal mouse serum, (2) non-specific $IgG_1$ mAb (such as 1E12 or any commercially available non-specific $IgG_1$ mAb) and (3) 1B2 mAb. Material bound to the 1B2 mAb column is eluted with 50 mM triethanolamine, and lyophilized. Using this approach, VAP-1 is isolated from tonsilar stroma. Other equivalent methods known in the art may be used.

Figure 2:
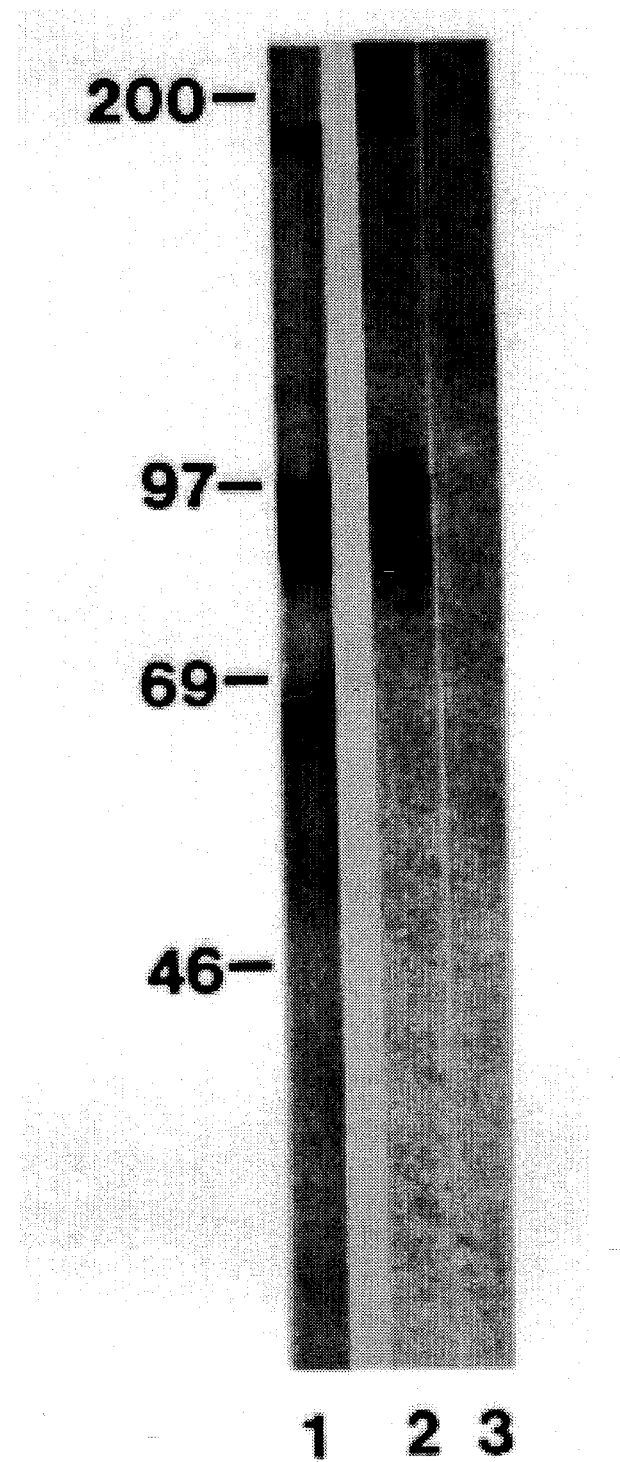
FIG. 2. VAP-1 is a 90 kD protein. Lane 1: silver staining immunopurified VAP-1. Lanes 2–3: $^{125}$I-labeled stromal cells of tonsil were immunoprecipitated with either mAb 1B2 (lane 2) or control mAb 3G6 (lane 3). The bands in the 180–200 kD area are not always present. Molecular weight standards are indicated on the left. Lymphocyte-depleted tonsillar extracts were solubilized in lysis buffer (150 mM NaCl, 10 mM Tris-base, 1.5 mM MgCl$_2$, 1% NP-40, 1 mM PMSF and 1% aprotinin) overnight at 4° C. The lysate was centrifuged at 10000 g for 30 min at 4° C. The supernatant was precleared by passing the lysate over a SEPHAROSE™ CL-4B (cross-linked beaded agarose) (Pharmacia, Sweden) column. Then it was sequentially applied to three CNBr-activated SEPHAROSE™-4B (beaded agarose) (Pharmacia) columns derivatized with normal mouse serum, with irrelevant IgG$_1$ mAb and with 1B2 mAb (5 mg/ml, 5 ml column volume). The column was washed extensively with the lysis buffer. Thereafter, the material bound to the 1B2 column was eluted with 50 mM triethanolamine, lyophilized, resolved in SDS-PAGE (7.5%, reduced) and visualized using silver staining.

As shown in Example 3 below, silver staining of immunoaffinity-purified VAP-1 and immunoprecipitates from surface-iodinated tonsil tissue fragments yield two different-sized species of VAP-1 when resolved on linear SDS-PAGE (7.5%, reduced), a major band of molecular weight 90 kD (100 kD under non-reducing conditions) and a 180–200 kD band (FIG. 2).

Figure 8A:
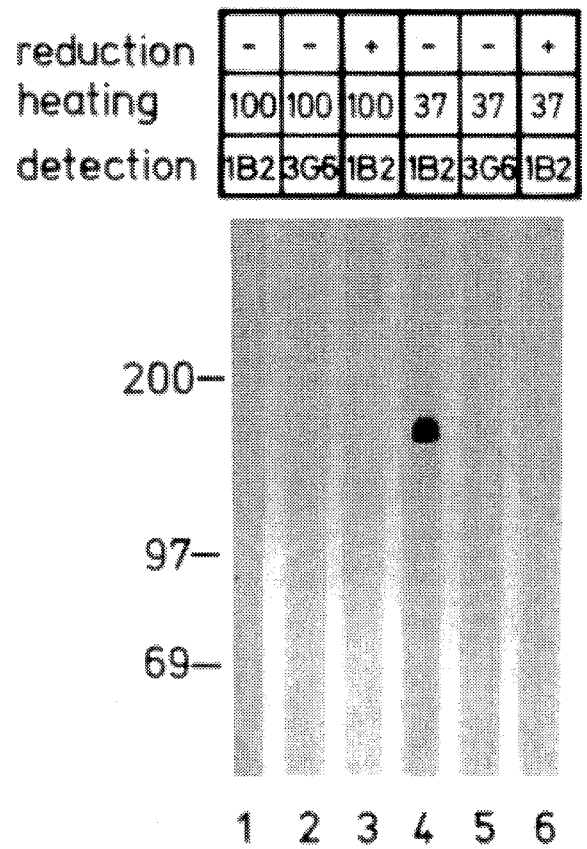
FIG. 8 (A–B). The 170 kD form is the major immunoreactive species of VAP-1. (A) (NH$_4$)$_2$SO$_4$-precipitated tonsil NP-40 lysate was subjected to different treatments prior to separation in SDS-PAGE and immunoblotting. Samples were analyzed without (reduction−) or with (reduction+)2-ME after boiling for 5 min at 100° C. (100) or heating for 20 min at 37° C. (37). MAb 1B2 only reacted with the 170 kD molecule under non-reducing conditions when boiling was omitted (lane 4). 3G6 is a negative control mAb. (B) In $^{35}$S-cysteine/$^{35}$S-methionine labeled tonsil organ culture, mAb 1B2 specifically precipitates a major 170 kD and a less prominent 90 kD form of VAP (arrows). M.w standards are indicated on the left. IP=immunoprecipitation.

The inventors used immunoblotting to determine which form of VAP-1 is the mature, immunoreactive molecule. Briefly, proteins from NP-40 lysates of stromal elements of tonsil are concentrated by precipitation with $(NH_4)_2SO_4$. Aliquots are mixed with equal volumes of Laemmli's sample buffer with or without reduction (5% 2-ME). Samples are subject to gentle heating (20 min, 37° C.) or boiling (5 min, 100° C.), and loaded on 5–12.5% SDS-PAGE gels. Resolved proteins are electroblotted onto nitrocellulose membranes using a liquid-based system at 4° C. VAP-1 is visualized using 1B2 and an enhanced chemiluminescence detection system. This experiment is described in more detail in Example 8. As the results show (FIG. 8), when reduced or non-reduced samples are boiled before loading on the gel, no signal is detectable. However, when the sample is not reduced and only mildly heated (20 min, 37° C.), a specific band at about 170 kD is seen (FIG. 8A, lane 4). VAP-1 reactivity to 1B2 is destroyed in the gently heated sample by reduction (FIG. 8A, lane 6). Thus, in tonsil, the mature 1B2 immunoreactive epitope is the 170 kD form of VAP-1.

Figure 8B:
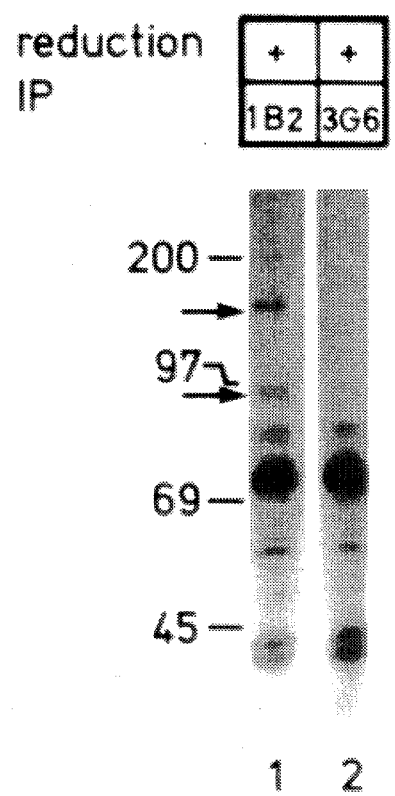

The inventors further discovered that the 170 kD form of VAP-1 can also be purified by metabolic labeling of tonsil tissue. Briefly, small tissue cubes are cut from tonsils and metabolically labeled with $^{35}S$-methionine/$^{35}S$-cysteine in an in vitro organ culture and NP-40 soluble proteins are then immunoprecipitated with 1B2. Antigens were eluted with Laemmli's sample buffer containing 5% 2-mercaptoethanol, and resolved in 5–12.5% SDS-PAGE. This method for purifying VAP-1 is described in detail in Example 8. Two 1B2 specific bands are detected (FIG. 8B). The size of the more prominent band at 170 kD corresponds to the 1B2-reactive band seen in the immunoblotting experiment described above, and thus represents the intact VAP-1 molecule. A 90 kD species is also specifically immunoprecipitated with 1B2. Thus, both the 170 and 90 kD forms of VAP-1 are actively produced in human lymphatic tissue.

To summarize, the 170 kD species is the mature form of VAP-1. This 170 kD protein is identical with the 180–200 kD form of VAP-1 seen in the analysis (Example 3) of immunoaffinity-isolates of 1B2-reactive material from tissue lysates and immunoprecipitates from small fragments of tonsil stroma subject to peroxidase-catalyzed surface labeling with $^{125}I$. The small difference in size is due to differences in gel systems (linear vs. gradient) and in sample treatment.

As detected using monoclonal antibody 1B2, in cells, VAP-1 is abundant in HEV-like venules in inflamed synovial membranes. VAP-1 is not present in infiltrating leukocytes or in any connective tissue component of the synovial stroma. In peripheral lymph node and tonsil, VAP-1 appears to be present in the majority of HEV. VAP-1 is highly localized at the luminal side of the endothelial cells. A granular staining of VAP-1 is seen in the endothelial cell cytoplasm, and also at the abluminal surface.

Especially in tonsil, VAP-1 levels greatly vary between different HEV, and a few individual HEV (with a typical plump morphology) completely lack VAP-1. In appendix, and in lamina propria of the gut, only a few faintly staining venules appear to be present. Weak expression of VAP-1 is found on dendritic-like cells in germinal centers and on smooth muscle cells of arteries, veins and bowel wall.

In contrast, VAP-1 is practically absent from the luminal surface of larger vessels. Like leukocytes in tissue sections, peripheral blood lymphocytes, monocytes, natural killer (NK) cells, granulocytes and isolated tonsillar leukocytes were all completely 1B2-negative in FACS analyses. T-lymphoblastoid (CCRF-CEM (CCL 119, ATCC)), B-lymphoblastoid (KCA and IBW-4), monocytic (U937 (CRL 1593, ATCC)), and leukemic (KG-1 (CCL 246, ATCC); KG-1a (CCL 246.1, ATCC) and K562 (CCL 243, ATCC)) cell lines all lacked VAP-1. Moreover, VAP-1 was absent from the surface of HUVEC, and 4 h or 20 h treatment with IL-1 (20 or 100 U/ml), TNF (200 U/ml) or LPS (0.1 or 1.0 µg/ml) could not induce its expression. Primary cultures of smooth muscle cells, fibroblasts, and keratinocytes and an epitheloid (HeLa) cell line did not express VAP-1.

Using the immunoblotting assay described above and in Example 8 below, the inventors have discovered that VAP-1 is a sialoglycoprotein and that the sialic acid residues are essential for lymphocyte binding, as the desialylated form of VAP-1 can no longer mediate lymphocyte binding, although it is still recognized by 1B2. In tonsil, both the 170 kD and the 90 kD species of VAP-1 are sialylated. Thus, the invention is further directed to a VAP-1 sialoglycoprotein capable of mediating lymphocyte binding to endothelial cells.

Figures 12A, 12B:
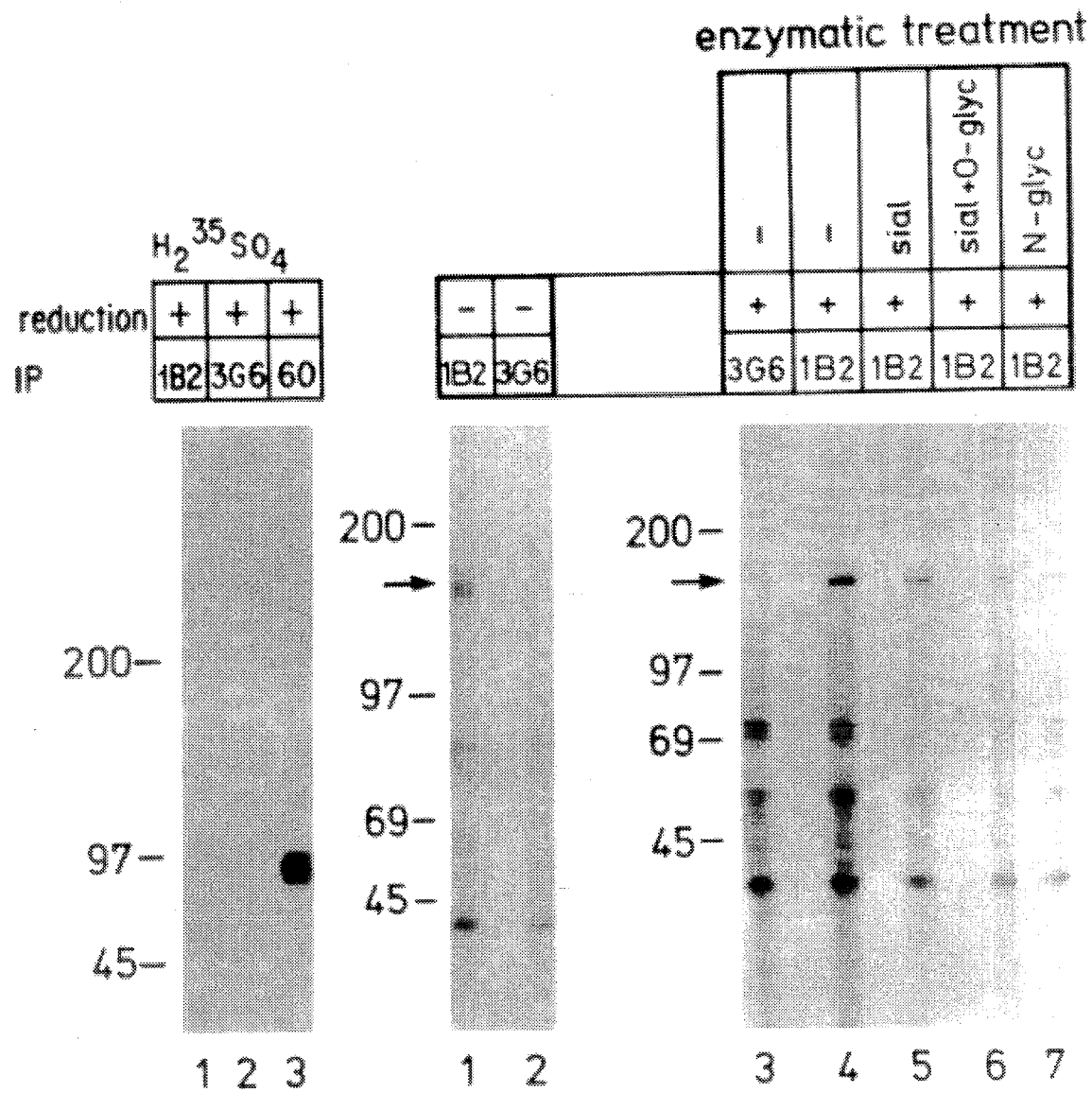
FIG. 12 (A–C). Biochemical characterization of VAP-1 in HEC. (A) HEC were labeled with $H_2{}^{35}SO_4$ and immunoprecipitations with mAbs 1B2, 3G6 (a negative control) and 60 (=Hermes-3 against CD44, a positive control) were performed. (B) HEC were metabolically labeled with $^{35}$S-methionine/$^{35}$S-cysteine and subjected to various treatments after immunoprecipitations. Under both non-reducing (lanes 1–2) and reducing (lanes 3–4) conditions mAb 1B2 detected a ~180 kD molecule. The electrophoretic mobility of this mAb 1B2 reactive molecule is not affected by sialidase (lane 5), sialidase digestion followed by O-glycanase (lane 6) or N-glycanase treatment (lane 7). (C) Metabolic inhibition of glycosylation does not affect the size of VAP-1. HEC were grown, starved and labeled with $^{35}$S-methionine/$^{35}$S-cysteine in the presence of indicated concentrations of tunicamycin (lanes 3–6) and benzyl-N-acetylgalactosaminide (concentration in mM, lanes 7–10), and subjected to immunoprecipitation (IP) with mAb 1B2 or 3G6 (a negative control). Arrows mark the specific 1B2 immunoprecipitate.
Figure 12C:
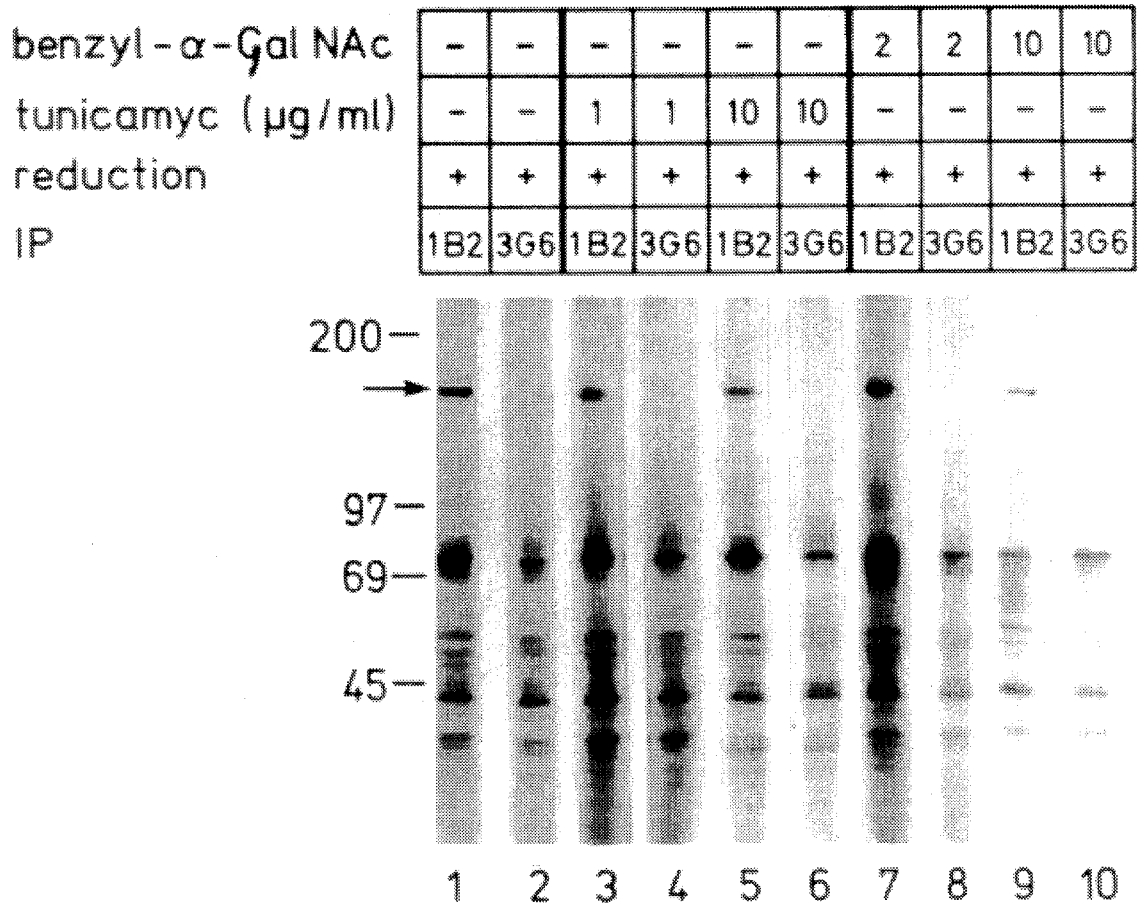

As discussed above, VAP-1 is absent from the surface of human umbilical vein endothelial cells (HUVEC) and an endothelial cell hybrid (HEC). However, in HEC and HUVEC, VAP-1 is present in the cytoplasm and not on the cell surface, whereas in tonsil HEV, VAP-1 is both lumenal and in discrete cytoplasmic granules. Moreover, in HEC, VAP-1 is not posttranslationally modified with sialic acids. The lack of surface expression of VAP-1 in HEC may be due to the defective sialylation of VAP-1 in these cells. The molecular mass of VAP-1 in HEC can be determined by metabolically labelling HEC with $^{35}$S-methionine/$^{35}$S-cysteine. NP-40 soluble proteins are then immunoprecipitated with 1B2 and resolved in 5–12.5% SDS-PAGE. The inventors have discovered that, under non-reducing conditions, a somewhat diffuse 180 kD band is seen (FIG. 12B, lane 1). Moreover, under reducing conditions (5% 2-ME), the electrophoretic mobility of VAP-1 antigen is not shifted although the band is sharper (FIG. 12B, lane 4). In HEC, no 90 kD form of VAP-1 is detectable.

Thus, the inventors have discovered that VAP-1 from HEC migrates at a different size than VAP-1 from tonsil (180 kD and 170 kD, respectively). Moreover, using glycosidase treatment, it was discovered that VAP-1 is sialylated in tonsil but not in HEC.

By the invention, sialylated VAP-1 capable of binding lymphocytes can be purified from tonsil HEV and desialylated VAP-1 can be purified from HEC or HUVEC according to conventional techniques.

Comparison of VAP-1 with the known endothelial cell molecules mediating leukocyte binding reveals several differences. Intercellular adhesion molecules-1 and-2 (ICAM-1 and ICAM-2), vascular cell adhesion molecule-1 (VCAM-1), E-selectin (ELAM-1) and P-selectin (CD62, PADGEM, GMP 140) are all expressed on the surface of HUVEC either basally or after induction by inflammatory mediators (Springer, T. A., *Nature* 346:425 (1990); Stoolman, L. M., *Cell* 56:907 (1989); Osborn, L., *Cell* 62:3 (1990); Pober and Cotran, *Transplantation* 50:537 (1990); Butcher, E. C., *Cell* 67:1033 (1991); de Fougerolles, A. R., et al., *J. Exp. Med.* 174:253 (1991); Osborn, L., et al., *Cell* 59:1203 (1989); Bevilacqua, M. P., et al., *Proc. Natl. Acad. Sci. USA* 84:9238 (1987); McEver, R. P., et al., *J. Clin. Invest.* 84:92 (1989); Hattori, R., et al., *J. Biol. Chem.* 264:7768 (1989); Wellicome, S. M., et al., *J. Immunol.* 144:2558 (1990); Pober, J. S., et al., *J. Immunol.* 137:1893 (1986); Dustin, M. L., et al., *J. Immunol.* 137:245 (1986)). In contrast, VAP-1 is neither constitutively expressed nor inducible by IL-1, TNFa or LPS treatments on the surface of HUVEC. Tissue distributions of these molecules are clearly distinct-also, the distribution is distinct when analyzed on parallel sections of tonsil (dam not shown). ICAMs stain the luminal surface of most large and small vessels and certain leukocytes (de Fougerolles, A. R., et al., *J. Exp. Med.* 174:253 (1991); Dustin, M. L., et al., *J. Immunol.* 137:245 (1986)). VCAM-1 and ELAM-1, on the other hand, only stain a few venules in inflamed tissues (Rice, G. E., et al., *J. Exp. Med.* 171:1369 (1990); Rice, G. E., et al., *Am. J. Pathol.* 138:385 (1991); Cotran, R. S., et al., *J. Exp. Med.* 164:661 (1986)). Instead, VAP-1 is strongly expressed on the vast majority of HEV at non-mucosal sites, and it is absent from all white cells and cell lines tested. The molecular weights of the known adhesion molecules are also clearly different from that of VAP-1, with the exception of ICAM-1 (ICAM-2 is a 60 kD, VCAM-1 110 kD, E-selectin 115 kD and P-selectin 140 kD molecule, Stoolman, L. M.,*Cell* 56:907 (1989); Osborn, L., *Cell* 62:3 (1990); and deFougerolles, A. R. et al., *J. Exp. Med.* 174:253 (1991)). Furthermore, VAP-1 is mainly involved in lymphocyte binding, while ICAMs, E- and P-selectin also efficiently mediate adhesion of polymorphonuclear leukocytes (Springer, T. A., *Nature* 346:425 (1990); Stoolman, L. M., *Cell* 56:907 (1989); Osborn, L., *Cell* 62:3 (1990); Pober and Cotran, *Transplantation* 50:537 (1990); Butcher, E. C., *Cell* 67:1033 (1991)). The only endothelial adhesion molecule described so far that is involved in lymphocyte binding in man and is not expressed on HUVEC is the MECA-79-defined antigen (Berg, E. L., et al., *J. Cell Biol.* 114:343 (1991)). However, it is a tissue-specific addressing of peripheral lymph nodes. Moreover, VAP-1 is not co-expressed in all MECA-79-positive venules, and mAb 1B2 does not recognize purified MECA-79 antigen.

Therefore, the expression pattern, function and molecular weight of VAP-1 indicate that it is not identical with any of the previously defined endothelial molecules involved in lymphocyte binding and that the degree of inflammation correlates to the level of VAP-1 expression in vivo. These results show that VAP-1 is relevant to understanding of the physiologic lymphocyte recirculation in man, and is especially valuable for dissecting the molecular mechanisms of tissue selective lymphocyte homing.

Figure 17:
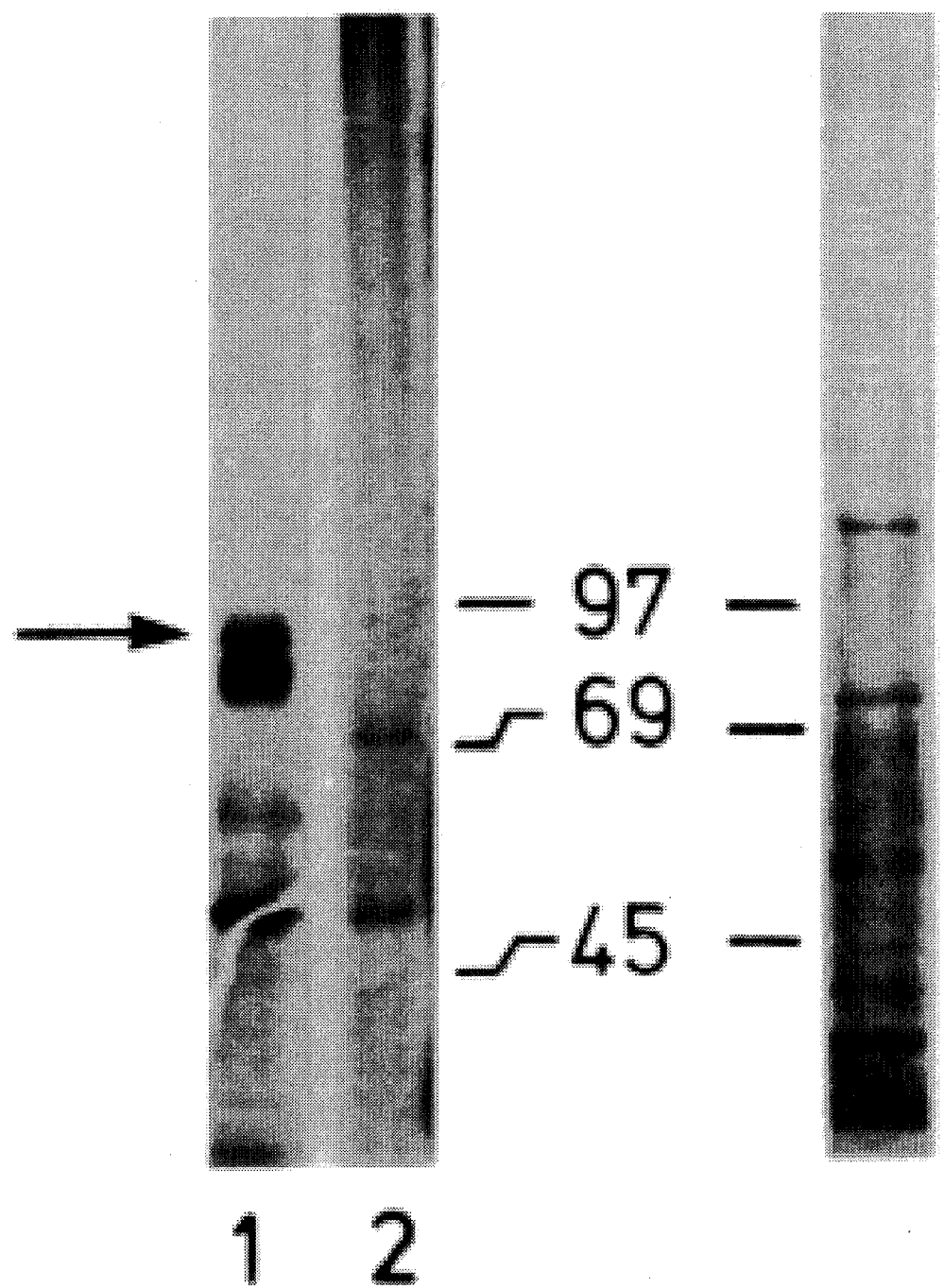
FIG. 17. mCyCAP specifically binds to mAb 1B2. MAb 1B2 was coupled to CnBr-activated SEPHAROSE™-4B (beaded agarose) beads (no tonsil lysate was applied to the column), and eluted with triethylamine (lane 1). For comparison, see FIG. 14A for the mAb 1B2 column with tonsil lysate. As controls, mAbs 4G4 (lane 2) against LVAP-2 (Airas et at., *J. Immunol.* 151:4228 (1993)), and 6E8 (lane 3) were analogously coupled, and tonsil lysate was run through the columns before elution. Eluted antigens were separated in SDS-PAGE and visualized by silver staining. Note that only mAb 1B2 column yielded the strong 90 kD band.

As discussed above, the N-terminus of the mCyCAP protein is a mimotope of VAP-1. The cDNA sequence of mCyCAP was published by Friedman et al., *PNAS (USA)* 90:6815–6819 (1993). This cDNA sequence predicted a protein with a stretch of amino acids having 100% identity with the amino acid sequence TEDGDMXLVN-GASANEGXVE [SEQ ID No. 2], which was previously described (Salmi and Jalkanen, Science 257:1407–1409 (1992), United States application Ser. Nos. 08/124,490 and 07/895,354) as being the partial amino acid sequence of the 90 kD form of VAP-1. The present inventors considered the possibility that the 90 kD 1B2-immunoreactive species obtained in affinity-purification might consist of two proteins: the 90 kD form of VAP-1 and a co-precipitating mCyCAP. The inventors reasoned that the mouse protein (mCyCAP) would have to bind to 1B2 during the production of the monoclonal antibody in the NS-1 cells, since no material of mouse origin is present during later purification stages. The expression of mCyCAP in NS-1 hybridoma cells can be confirmed using reverse transcriptase polymerase chain reaction (PCR). Moreover, in another experiment, two identical CnBr-activated SEPHAROSE™-4B (beaded agarose) columns coupled with 1B2 are used: to one human tonsil lysate is applied and to the other no lysate is added (empty column). After elution, samples from both columns are separated by SDS-PAGE and the proteins visualized by silver staining. The prominent 90 kD band was observed both from the lysate containing (FIG. 14a) and the empty column (FIG. 17, lane 1 ). Moreover, the 90 kD proteins from both columns have the same N-terminal amino acid sequence. Thus, mCyCAP is also contained in the 1B2-immunoreactive 90 kD fraction and the amino acid sequence previously described as being the partial amino acid sequence of VAP-1 is actually attributable to mCyCAP. These findings led to the discovery by the present inventors that mCyCAP is a mimotope of VAP-1 and that a synthetic peptide from the N-terminus of mCyCAP is capable of raising VAP-1-specific antibodies that antagonize lymphocyte binding to endothelial cells.

Uses of VAP-1 and VAP-1 Binding Compounds

The present invention further relates to a diagnostic reagent for the detection of VAP-1 protein and VAP-1 positive cells, in samples taken from the human or animal body. Such a reagent may be a VAP-1-binding compound. VAP-1-binding compounds include an antibody, preferably a monoclonal antibody, with specificity for the VAP-1 protein, or a VAP-1-reactive fragment of said antibody, labelled, if desired, with a substance which permits the detection of binding of the antibody to the isolated VAP-1, or cells that express VAP-1 on their surface. Such diagnostic composition may be provided in a kit, such kit providing, in separate containers, (a) an antibody, preferably a monoclonal antibody, with specificity for VAP-1, or a biologically active derivative of said antibody, preferably labelled with a substance which permits detection of binding of the antibody to VAP-1 antigen; and (b) purified VAP-1 protein, to provide a standard for evaluation of the assay results.

VAP-1-specific antibodies can be raised against VAP-1 itself or against a mimotope of VAP-1.

In another aspect, the present invention is directed to a method of lessening or treating infection or inflammation, in-vivo, in the human or animal body, by administering, to a human or animal patient in need of such treatment, efficacious levels of a VAP-1-binding compound. Suitable VAP-1-binding compounds include antibodies, preferably monoclonal antibodies, with specificity for VAP-1 as described above.

The term "treatment" or "treating" is intended to include the administration of VAP-1-binding compounds to a subject for purposes which may include prophylaxis, amelioration, prevention or cure of disorders mediated by VAP-1 adhesion events. The particular VAP-1-binding molecules that are the subject of the methods of the invention are purified native and recombinant VAP-1-binding proteins, such as antibodies or other molecules.

When administered to a patient, the reagent of the invention may be formulated in any manner which makes it suitable for parenteral, nasal, enteric or rectal administration. Thus, the reagent may be in the form of, for instance, an injectable formulation, aerosol formulation, suspension, solution, enema, etc. The reagent may be formulated with pharmaceutically acceptable excipients or vehicles, e.g., isotonic saline, in accordance with conventional pharmaceutical practice. The dosage level of the reagent will be sufficient to provide an anti-inflammatory effect by the blocking of VAP-1 adhesion events in the patient.

The reagent of the invention is suitable for diagnosing or treating any condition involving a VAP-1 adhesion-mediated increased inflammatory reaction. Thus, the reagent is useful for diagnosing or treating such conditions as arthritis, local infections, dermatoses, inflammatory bowel diseases, autoimmune diseases, psoriasis, atopic eczema, lichen ruber planus, Crohn's disease, ulcerative colitis, etc.

In one embodiment, efficacious levels of VAP-1-binding compounds are administered so as to provide therapeutic benefits against the secondary harmful inflammatory effects of inflammation. By an "efficacious level" of a VAP-1-binding compound is meant a level in which the toxic effects of VAP-1 mediated events are, at a minimum, ameliorated. By "excessive" host VAP-1-mediated events are meant an level of VAP-1 mediated adhesion events in the subject which exceeds the norm for the healthy medical state of the subject. By "secondary" tissue damage or toxic effects is meant the tissue damage or toxic effects which occur to otherwise healthy tissues, organs, and the cells therein, due to the presence of excessive VAP-1-mediated adhesion events, including as a result of a "primary" stimulus elsewhere in the body.

In the methods of the invention, infusion of VAP-1-binding compounds, such as, for example, anti-VAP-1 antibodies or antibodies against a mimotope of VAP-1, into a patient, results in a binding of such antibodies to the patient's cells that express VAP-1 on their surface, such as synovial HEV, peripheral lymph node HEV and tonsil HEV so as to prevent their adhesion to other cells by VAP-1 binding, thus preventing or inhibiting lymphocyte adherence to such tissues and cells, and thus preventing undesired lymphocyte trafficking or influx into the affected tissues or organs, thus preventing undesired inflammatory responses that arose from VAP-1 directed leukocyte trafficking and leukocyte extravasation.

Accordingly, the pharmaceutical compositions of the invention provide for compositions containing VAP-1 binding compounds, in amounts sufficient to antagonize (fully or partially) the patient's native VAP-1 binding to biological targets of VAP-1 in such patient, and specifically to lymphocytes.

VAP-1 binding compounds may be conjugated, either chemically or by genetic engineering, to fragments of other agents which provide a targeting of such VAP-1-binding compounds to a desired site of action. Alternatively, other compounds may be conjugated, either chemically or by genetic engineering, to the VAP-1-binding compound, so as to enhance or provide additional properties to such VAP-1-binding compound, especially properties which enhance the compound's ability to promote relief of VAP-1 adhesion-mediated toxic effects.

Amounts and regimens for the administration of VAP-1-binding compounds can be determined readily by those with ordinary skill in the clinical art of treating inflammation-related disorders such as arthritis and tissue injury. Generally, the dosage of VAP-1-binding compound treatment will vary depending upon considerations such as: type of VAP-1-binding compound employed; age; health; medical conditions being treated; kind of concurrent treatment, if any, frequency of treatment and the nature of the effect desired; extent of tissue damage; gender; duration of the symptoms; and, counterindications, if any, and other variables to be adjusted by the individual physician. A desired dosage can be administered in one or more applications to obtain the desired results. Pharmaceutical compositions containing the VAP-1 binding compound of the invention, such as anti-VAP-1 antibody or anti-mimitope of VAP-1 antibody, may be provided in unit dosage forms.

The pharmaceutical compositions containing the VAP-1 binding compounds of the invention can be administered in any appropriate pharmacological carrier for administration. They can be administered in any form that effects prophylactic, palliative, preventative or curing conditions of VAP-1 mediated events in humans and animals. For the purpose of definition, it is intended that the expression "a method of treatment" of a disease, and like expressions, throughout the specification and claims, be taken to include a method for the prevention of such disease.

Preparations of the VAP-1-binding proteins of the invention for parenteral administration includes sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The VAP-1-binding compounds of the invention may also be administered by means of pumps, or in sustained-release form, especially, when the primary injury is prolonged or delayed rather an acute. An example in which the primary injury is often prolonged or delayed rather than acute is an infection or sprain wherein the damage to the tissue or muscle is not revealed (or persists) until days after the primary infection or damage. The VAP-1-binding molecules of the invention may also be delivered to specific organs in high concentration by means of suitably inserted catheters, or by providing such molecules as a part of a chimeric molecule (or complex) which is designed to target specific organs.

Administration in a sustained-release form is more convenient for the patient when repeated injections for prolonged periods of time are indicated. For example, it is desirable to administer the VAP-1-binding proteins of the invention in a sustained-release form when the methods of the invention are being used to treat a genetic or chronic inflammatory disease that is based upon an VAP-1-related disorder so as to maximize the comfort of the patient.

The VAP-1-binding compound of the invention can be employed in dosage forms such as tablets, capsules, powder packets, or liquid solutions for oral administration if the biological activity of the VAP-1-binding compound is not destroyed by the digestive process and if the characteristics of the compound allow it to be absorbed across the intestinal tissue.

The pharmaceutical compositions of the present invention are manufactured in a manner which is in itself know, for example, by means of conventional mixing, granulating, dragee-making, dissolving, lyophilizing or similar processes. The compositions of the present invention, in and of themselves, find utility in the control of VAP-1-induced physiological damage, be it chronic or acute. The compositions of the invention obviate the body's own mechanisms for recognizing VAP-1 adhesion to its maximum potential.

In intravenous dosage form, the compositions of the present invention have a sufficiently rapid onset of action to be useful in the acute management of potential tissue damage.

Additionally, a low potency version is useful in the management of mild or chronic VAP-1-related disorders.

In addition, the diagnostic compositions of the present invention provide requisite reagents for the laboratory assay of VAP-1 levels in a human's or in an animal's bloodstream or extracellular fluids. The inventors have discovered that there is a soluble form of VAP-1 in bodily fluids. Thus, another embodiment of the present invention is directed to detecting VAP-1 levels in a patient comprising:

(1) removing a sample of bodily fluid from the patient;

(2) exposing said sample to a VAP-1-specific antibody; and (3) detecting VAP-1-specific antibody binding to VAP-1 present in said sample.

Samples of bodily fluid can be obtained according to conventional techniques from sources such as, for example, plasma, serum and synovioum. As discussed above, VAP-1-specific antibodies can be polyclonal or monoclonal and can be raised against VAP-1 itself or against a mimotope of VAP-1. Preferably, the VAP-1-specific antibody will be labelled with a substance which permits the detection of the binding of the antibody to VAP-1.

VAP-1-binding proteins that are substantially free of natural contaminants can be isolated and purified from their natural or recombinant sources in accordance with conventional conditions and techniques in the art previously used to isolate such proteins, such as extraction, precipitation, chromatography, affinity chromatography, electrophoresis, or the like.

The following examples are merely intended to illustrate the present invention and not in any way to limit its scope.

EXAMPLES

Example 1

Tissue distribution of VAP-1

The tissue distribution of VAP-1 was determined by immunoperoxidase staining of cryostat sections. The sections were incubated with primary antibodies (1B2 and 3G6, a control mouse $IgG_1$ mAb against chicken T cells) for 30 min. After two washings in phosphate buffered saline (PBS, 8 g NaCl, 1.21 g $K_2HPO_4$ and 0.34 g $KH_2PO_4$ per liter, pH 7.2), peroxidase-conjugated sheep anti-mouse IgG (Dakopatt, Denmark) in PBS containing 5% AB-serum was added for 30 min. Next, 3'3'-diaminobenzidine hydrochloride in PBS containing 0.03% hydrogen peroxide was used as a chromogen After the staining, the sections were counterstained with hematoxylin. For immunofluorescence staining, 3 µm cryostat sections were overlaid with primary antibodies and FITC-conjugated sheep anti-mouse IgG (Sigma, St. Louis) was used as a second-stage reagent.

Figure 1B:
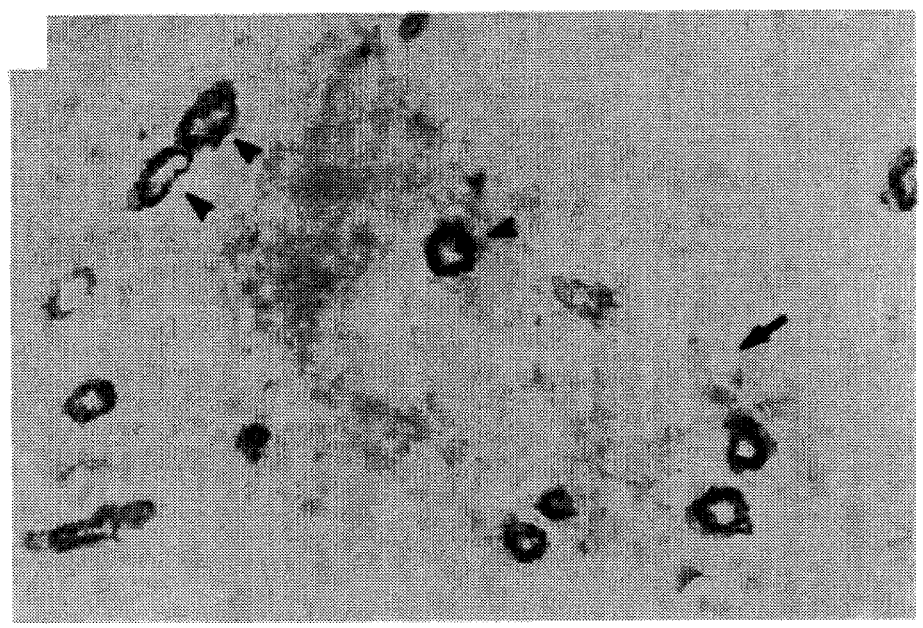
Figure 1C:
Figure 1D:
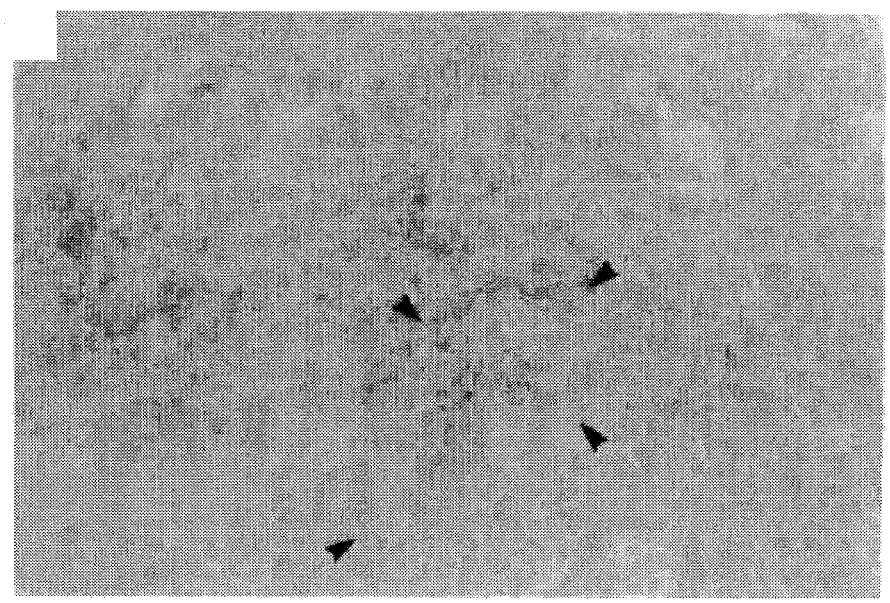

Immunohistological stainings revealed that monoclonal antibody 1B2 strongly stained HEV-like venules in inflamed synovial membranes (FIG. 1A). No staining was observed in infiltrating leukocytes nor in any connective tissue component of the synovial stroma. The antigen recognized by mAb 1B2 was named VAP-1 (for Vascular Adhesion Protein-1). In peripheral lymph node and tonsil, mAb 1B2 reacted with the majority of HEV (FIG. 1B). VAP-1 was intensely expressed at the luminal side of the endothelial cells (FIG. 1C). A granular staining was seen in the endothelial cell cytoplasm, and also the abluminal surface was mAb 1B2 positive. Especially in tonsil, the staining intensity notably varied between different HEV, and few individual HEV with a typical plump morphology were 1B2-negative (FIG. 1D). In appendix and in lamina propria of the gut, only few faintly staining venules were detected. Weak expression of VAP-1 was also seen on dendritic-like cells in germinal centers and on smooth muscle cells of arteries, veins and bowel wall. In contrast, VAP-1 was practically absent from the luminal surface of larger vessels. Like leukocytes in tissue sections, peripheral blood lymphocytes, monocytes, NK cells, granulocytes and isolated tonsillar leukocytes were all completely 1B2-negative in FACS analyses. T-lymphoblastoid (CCRF-CEM), B-lymphoblastoid (KCA, IBW-4), monocytic (U937) and leukemic (KG-1, KG-1a, K 562) cell lines all lacked VAP-1. Moreover, VAP-1 was absent from the surface of human umbilical vein endothelial cells (HUVEC), and 4 h or 20 h treatments with IL-1 (20,100 U/ml), TNF-α (200 U/ml) or LP5 (0.1, 1.0 μg/ml) could not induce its synthesis. Primary cultures of smooth muscle cells, fibroblasts and keratinocytes, and an epithelioid (HeLa) cell line did not express VAP-1.

Example 2

Intracellular localization of VAP-1

In addition to the tissue localization experiments described in Example 1, the intracellular localization of VAP-1 was further studied by confocal microscopy of thick sections (15 μm) cut from tonsils. Sections were incubated with mAb 1B2 or 3G6 for 15 min, washed twice with PBS and overlaid with FITC-conjugated sheep anti-mouse Ig for another 15 min. Thereafter, samples were mounted in glycerol containing 10% PBS and phenylediamine as anti-fading agent prior to analysis by confocal microscope. By microscopic inspection it was readily discernible that VAP-1 is present on the luminal surface of HEV as well as in discrete granules within the cytoplasm. The identity of these granules is currently unclear, but in two-color immunofluorescence stainings using mAb 1B2 and antibody against Factor VIII, the granules did not co-localize. Thus, VAP-1 positive granules are not Weibel-Palade bodies of endothelial cells, known to reside the endothelial cell adhesion molecule, P-selectin.

Example 3

Determination of the molecular weight of VAP-1

Lymphocyte-depleted tonsillar extracts were solubilized in lysis buffer (150 mM NaCl, 10 mM Tris-base, 1.5 mM $MgCl_2$, 1% NP40, 1 mM PMSF and 1% aprotinin) overnight at 4° C. The lysate was centrifuged at 10000 g for 30 min at 4° C. The supernatant was precleared by passing the lysate over a SEPHAROSE™ CL-4B (cross-linked beaded agarose) (Pharmacia, Sweden) column. Then it was sequentially applied to three CNBr-activated SEPHAROSE™-4B (beaded agarose) (Pharmacia) columns derivatized with normal mouse serum, with irrelevant $IgG_1$ mAb and with 1B2 mAb (5 mg/ml, 5 ml column volume). The column was washed extensively with the lysis buffer. Thereafter, the material bound to the 1B2 column was eluted with 50 mM triethanolamine, lyophilized, resolved in SDS-PAGE (7.5%, reduced) and visualized using silver staining.

For iodine labeling, lymphocyte-depleted tonsillar extracts were digested in RPMI 1640 containing 100 U/ml collagenase (type Ii from *Clostridium histolyticum*, Sigma) 10% fetal calf serum (FCS), antibiotics, and 10 mM Hepes for 1 hour at 37° C. with gentle stirring. After the collagenase digestion, cells were washed in HBSS, and surface-labeled with $^{125}I$ using the lactoperoxidase method. Iodinated cells were lysed with the lysis buffer, and the lysate was clarified by centrifugation at 10000 g for 15 min. The lysate was precleared for 16 h at 4° C. with CNBr-activated SEPHAROSE™ (beaded agarose) coupled to normal mouse serum. Immunoprecipitations were carried out with CNBr-activated SEPHAROSE™-4B (beaded agarose) beads conjugated with mAbs 1B2 or 3G6. The samples were analyzed using 7.5% SDS-PAGE under reducing (2-mercaptoethanol) conditions.

To determine the molecular weight of VAP-1, affinity-isolated molecule from tonsillar stroma was subjected to SDS-PAGE. Silver staining of the gel revealed a major band of apparent molecular weight of 90 kD under reducing conditions (FIG. 2). VAP-1 migrated slightly slower under non-reducing conditions (Mr 100 kD). Analyses of immunoprecipitates from iodinated stromal cells of tonsil confirmed the reactivity of mAb 1B2 with a 90 kD molecule (and a slightly smaller degradation product) (FIG. 2). Also a 180–200 kD band was sometimes visible.

Example 4

Binding of lymphocytes to tonsil, peripheral lymph node (PLN), synovial, and appendix HEV and binding of granulocytes to tonsil HEV The tissue distribution of VAP-1 on endothelial cells in vivo suggested that it might function as a specific recognition element for leukocytes. Therefore, the functional role of VAP-1 in HEV-binding was studied by using the modified Stamper-Woodruff in vitro assay (Jalkanen and Butcher, *Blood* 66:577 (1985)). The details of this technique have been described earlier (Jalkanen and Butcher, *Blood* 66:577 (1985)). Briefly, freshly cut frozen sections from human tonsil, synovium, appendix and peripheral lymph node were incubated with 1B2 or 3G6 supernatants for 30 min at 7° C. with mild rotation. Ficoll-isolated lymphocytes ($3\times10^6$/section) in HBSS containing 5% FCS and 10 mM Hepes were then added and incubation was continued for 30 min. After incubation, non-adherent cells were gently tipped off and the adherent cells were fixed overnight in cold PBS containing 1% glutaraldehyde. Cells bound to HEV on four to six sections per tissue per sample were counted (minimum of 100 HEV) single blind. When determining granulocyte binding, the assay was done similarly, with the exception that granulocytes (isolated using Histopaque 1119, Sigma) were kept in $Ca^{2+}$—$Mg^{2+}$—free HBSS, until just before application onto the sections.

Figure 3:
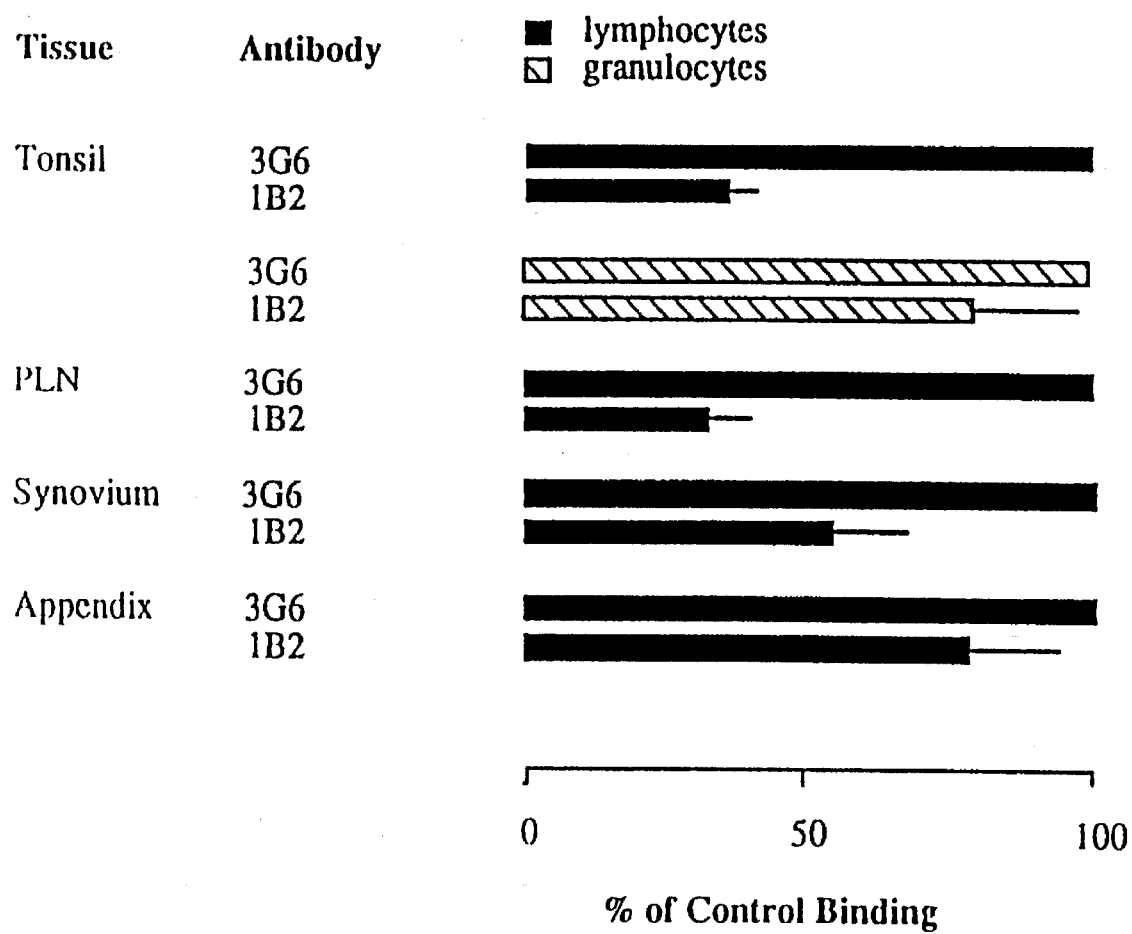
FIG. 3. VAP-1 is involved in lymphocyte binding to HEV. Binding of lymphocytes to tonsil, peripheral lymph node (PLN), synovial, and appendix HEV and binding of granulocytes to tonsil HEV were assessed in the presence and absence of mAb 1B2 using the in vitro frozen section assay. Results of three independent experiments are presented as percentages of control binding with standard errors (100%= number of bound cells on 3G6 (negative control) treated sections).
Figure 4A:
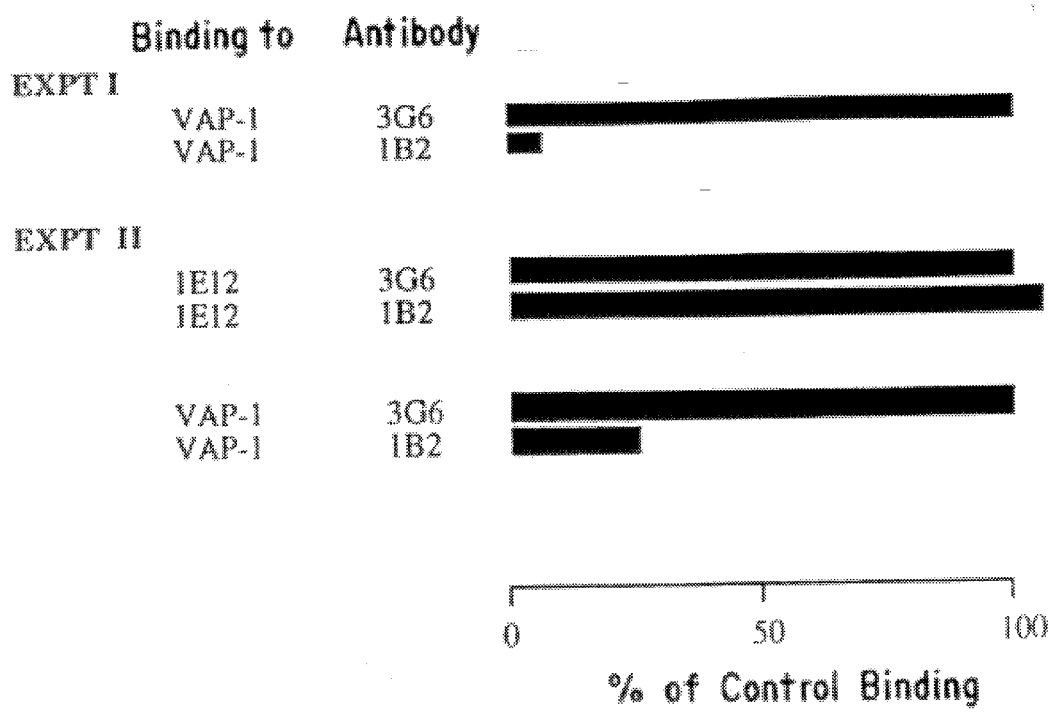
FIG. 4 (A–C). Isolated VAP-1 supports lymphocyte binding. Immunopurified VAP-1 and control proteins (1E12; an unrelated endothelial cell molecule that supports lymphocyte binding, and BSA) were absorbed on glass, and lymphocyte binding was determined. (A) Results from two independent experiments are presented as percentages from control binding (100%=number of cells bound to plate-bound VAP-1 or 1E12 after mAb 3G6 treatment). Nonspecific background (binding to BSA) is subtracted from all analyses. (B) Lymphocyte binding to VAP-1-coated well in the presence of mAb 3G6. (C) Lymphocyte binding to VAP-1-coated well in the presence of mAb 1B2. VAP-1 and 1E12 were affinity purified from tonsillar extracts as indicated in FIG. 2. Purified VAP-1, 1E12 and heat-inactivated BSA were diluted in 20 mM Tris-HCl, pH 7.4, 150 mM NaCl, 2 mM MgCl$_2$, 2 mM CaCl$_2$ with 0.01% β-octyl glucopyranoside as detergent. Proteins were absorbed onto glass wells (Lab-Tek chamber slides, Nunc) for 16 h at +4° C. After blocking in PBS containing 1 mg/ml BSA for 30 min at room temperature, 1B2 or 3G6 supernatants were added into wells and incubation was continued for 30 min at room temperature. Meanwhile, freshly isolated peripheral blood mononuclear cells were incubated in RPMI 1640 containing 10% FCS and 10 mM Hepes for 1 hour at 37° C. in tissue culture bottles to deplete the plastic adherent monocytes. Non-adherent lymphocytes (1.8×10$^6$ cells/well) in 100 μl RPMI 1640 were applied into each well. After 30 min incubation at 37° C., the non-adherent cells were removed by flicking. The tops of the wells were removed, the slides were washed by gentle stream of PBS, and fixed in cold PBS containing 1% glutaraldehyde. Thereafter, the cells were stained using the Diff-Quick stains. The bound cells were quantitated by visually scoring the number of cells in each well (total area of 50 mm$^2$/sample).
Figure 4B:
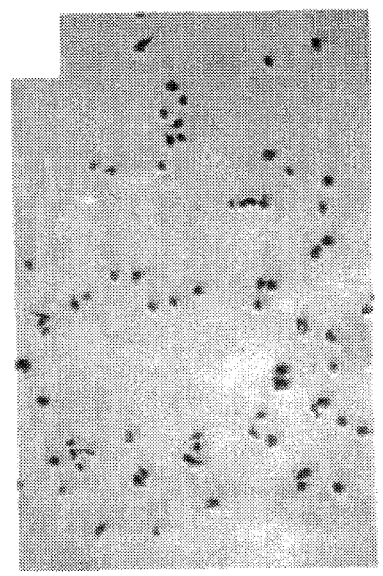
Figure 4C:
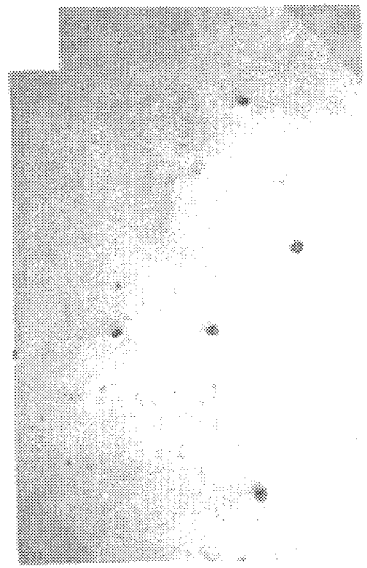

Pretreatment of the frozen sections with mAb 1B2 inhibited lymphocyte binding to HEV (FIG. 3). The inhibitory effect was most pronounced in tonsil and peripheral lymph node, but binding to synovial HEV was also significantly reduced. Lymphocyte binding to appendix HEV and granulocyte binding to tonsil HEV were less affected (FIG. 3). These findings indicate that VAP-1 either mediates or associates closely with endothelial cell elements mediating lymphocyte recognition of peripheral lymph node, tonsil and synovial HEV. To directly evaluate the involvement of VAP-1 in lymphocyte-endothelial cell interaction, binding of lymphocytes to affinity-isolated VAP-1 was analyzed (FIG. 4). Lymphocytes adhered efficiently to plate-bound VAP-1. Lymphocyte binding to VAP-1 was specifically inhibited with mAb 1B2, but not with a control mAb 3G6. MAb 1B2 did not prevent lymphocyte binding to another unrelated endothelial cell molecule (FIG. 4).

Tissue distribution and HEV-binding results suggest that VAP-1 is mainly involved in lymphocyte trafficking to peripheral lymph node, tonsil and synovium. Interestingly, in tonsil, lack of VAP-1 expression defines a minor subset of postcapillary venules, which are morphologically indistinguishable from 1B2-positive ones. Since tonsils are intimately associated to the gastrointestinal tract, they may contain HEV-specificities of both mucosal (VAP-1 negative)

and peripheral lymph node (VAP-1 positive) types. It remains to be determined how the phenotypic difference in VAP-1 expression correlates to lymphocyte binding capacity of each individual HEV. The scarcity of VAP-1 in mucosal lymphoid organs implies that this endothelial antigen may be differentially regulated in distinct lymphocyte recognition systems. Moreover, the degree of inflammation correlates to the level of VAP-1 expression in vivo.

Example 5

Assay for the Effect of 1B2 on the Binding of Cells to VAP-1

VAP-1 and 1E12 were affinity purified from tonsillar extracts as described in Example 2. Purified VAP-1, 1E12 and heat-inactivated BSA were diluted in 20 mM Tris-HCl, pH 7.4, 150 mM NaCl, 2 mM $MgCl_2$, 2 mM $CaCl_2$ with 0.01% β-octyl glucopyranoside as detergent. Proteins were absorbed onto glass wells (Lab-Tek chamber slides, Nunc) for 16 h at +4° C. After blocking in PBS containing 1 mg/ml BSA for 30 min at room temperature, 1B2 or 3G6 supernatants were added into wells and incubation was continued for 30 min at room temperature. Meanwhile, freshly isolated peripheral blood mononuclear cells were incubated in RPMI 1640 containing 10% FCS and 10 mM Hepes for 1 hour at 37° C. in tissue culture bottles to deplete the plastic adherent monocytes. Nonadherent lymphocytes ($1.8×10^6$ cells/well) in 100 μl RPMI 1640 were applied into each well. After 30 min incubation at 37° C., the non-adherent cells were removed by flicking. The tops of the wells were removed, the slides were washed by gentle stream of PBS, and fixed in cold PBS containing 1% glutaraldehyde. Thereafter, the cells were stained using the Diff-Quick stains. The bound cells were quantitated by visually scoring the number of cells in each well (total area of 50 $mm^2$/sample).

Example 6

Determination of VAP-1 in Clinical Samples Showing Inflammatory Response

Normal peripheral lymph node, gut, and heart samples were freshly obtained from surgical operations, and kidney samples from organ donors. Tonsils were from tonsillectomies and other tissues were from autopsy samples. All these specimens were histopathologically determined to be non-inflamed. Inflamed specimens were obtained from skin punch biopsies of patients suffering from chronic dermatoses (psoriasis, atopic eczema, lichen ruber planus). Control biopsies from macroscopically uninvolved areas of the same patients were also taken. Inflamed gut specimens were from patients with inflammatory bowel disease (Crohn's disease, ulcerative colitis) that underwent surgery for therapeutic purposes. Synovial specimens were from synovectomies.

Samples were stained with immunoperoxidase as described in Example 1. Briefly, acetin-fixed frozen sections were incubated sequentially with primary antibodies (culture supernatants or 50 μg/ml purified immunoglobulin) and with appropriate peroxidase conjugated second-stage reagents and the color reaction was developed using $H_2O_2$ an diaminobenzidine as the substrate. VAP-1 expression in bowel and skin samples (normal and inflamed) was analyzed by two independent readers from coded samples without knowledge of the diagnosis.

Figure 5A:
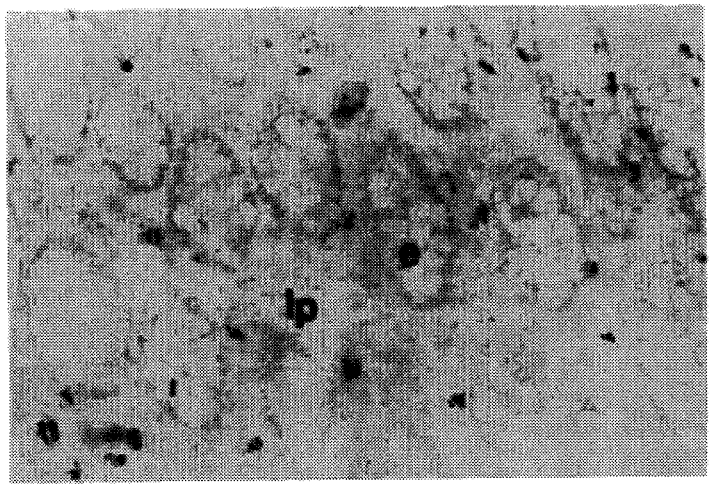
FIG. 5 (A–C). VAP-1 is up-regulated in the inflamed gut. (A) In normal gut, only a few faintly positive vessels in the lamina propria are observed. In this area, venules are practically negative for VAP-1. (B) In the inflamed gut (ulcerative colitis), numerous VAP-1 positive venules (arrows) are seen both in lamina propria and (C) in organized lymphoid follicles. Endogenous peroxidase-containing cells (mast cells) show non-specific reactivity. e, epithelial cells of the gut; lp, lamina propria. Magnification ×250.
Figure 5B:
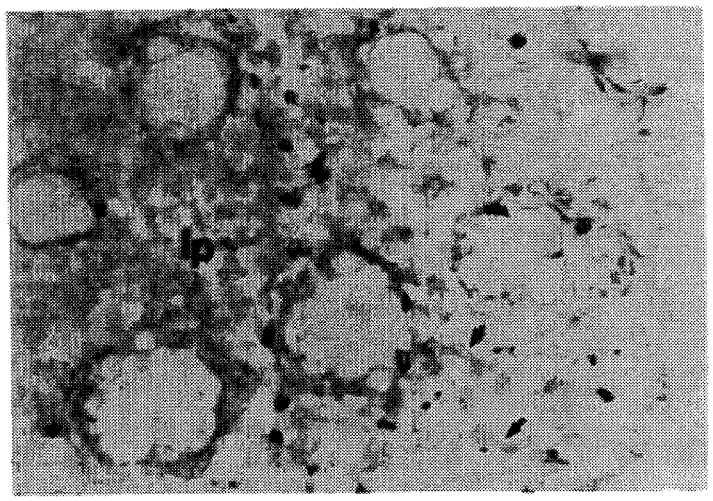
Figure 5C:
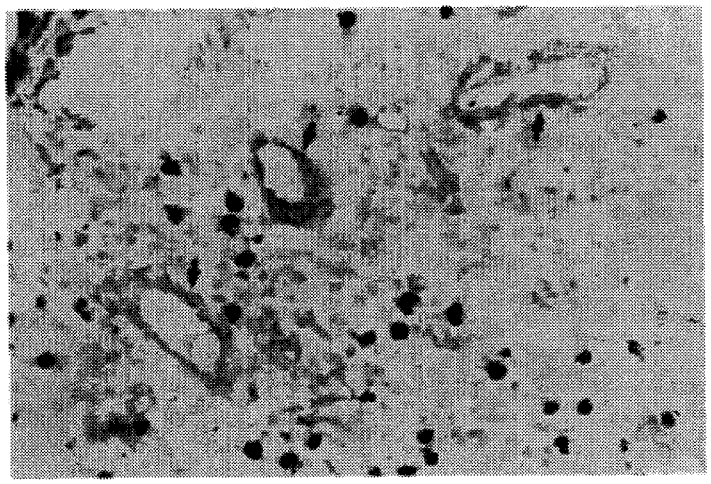
Figure 6A:
FIG. 6 (A–C). VAP-1 induction in chronic dermatoses. Skin biopsies from normal area (A) and from psoriatic lesion (B) of the same patient reveal induction of VAP-1 in dermal vessels (arrowheads) at site of inflammation. Perivascular leukocyte infiltrates can be seen around VAP-1 positive venules. e, epidermis,. Magnification ×200. (C) Expression of VAP-1 (scored from + to ++++) in normal and diseased skin was determined in the paired biopsies (non-involved and involved) from the same patients. In the parenthesis is shown the number of patients belonging to each group.
Figure 6B:
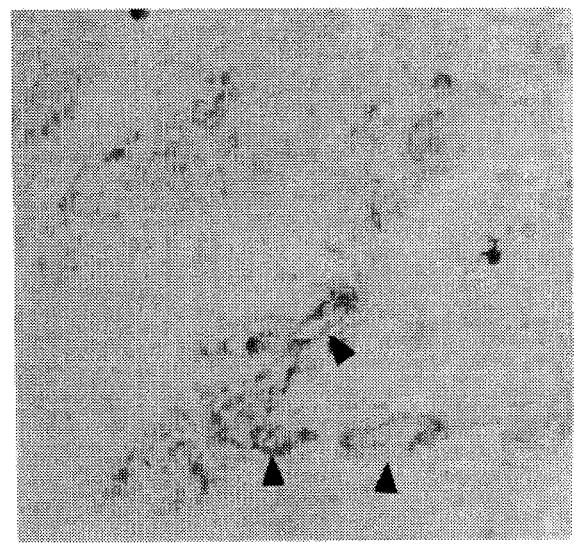
Figure 6C:
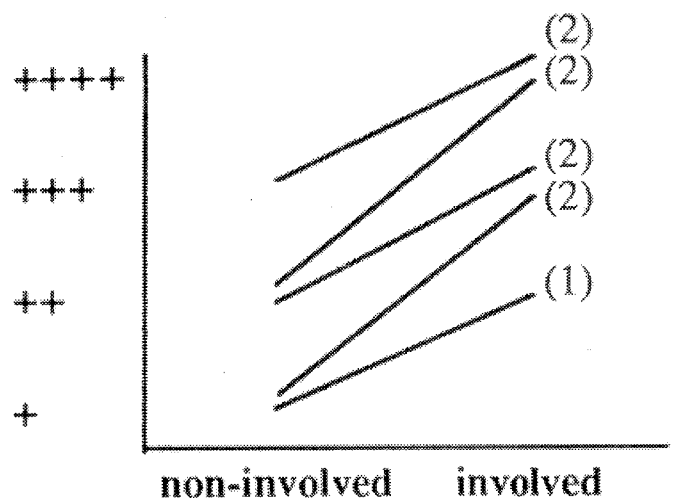

As noted in Example 1, VAP-1 is only expressed at low level in some venules of normal non-inflamed gut (FIG. 5A). In contrast, gut specimens from patients with inflammatory bowel diseases displayed a markedly increased expression of VAP-1 (FIGS. 5B and 5C and Table 1). VAP-1 was induced both in the flat-walled venules of the lamina propria and in the HEV-like venules in organized lymphatic follicles (Peyer's patches). Also in skin, chronic inflammation was accompanied with increased synthesis of VAP-1 (FIGS. 6A and B). To exclude any effects of interindividual variations in the results, one sample from the dermatosis lesion and a control sample from uninvolved skin area of the same patient were simultaneously biopsied and stained. Also in these specimens, number of VAP-1 positive venules in the upper dermis was higher in the inflamed sample than in the sample from the control area. Moreover, prominent perivascular leukocyte 5 infiltrates were constantly associated with VAP-1 positive vessels.

TABLE 1

Induction of VAP-1 in Inflammatory Bowel Diseases

| Specimen | n | VAP-1 | | | | |
|---|---|---|---|---|---|---|
| | | − | + | ++ | +++ | ++++ |
| Normal | 9 | 0 | 5 | 3 | 1 | 0 |
| Crohn | 7 | 0 | 0 | 2 | 3 | 2 |
| Ulc col | 7 | 0 | 0 | 0 | 5 | 2 |

Bowel specimens were from patients operated on for Crohn's disease, ulcerative colitis and tumors (uninvolved area of tumor samples represents "normal" samples). Number of VAP-1 positive venules in each sample was scored from − to ++++.

Example 7

VAP-1 Mediates Binding to the Inflamed Mucosa

Figure 7:
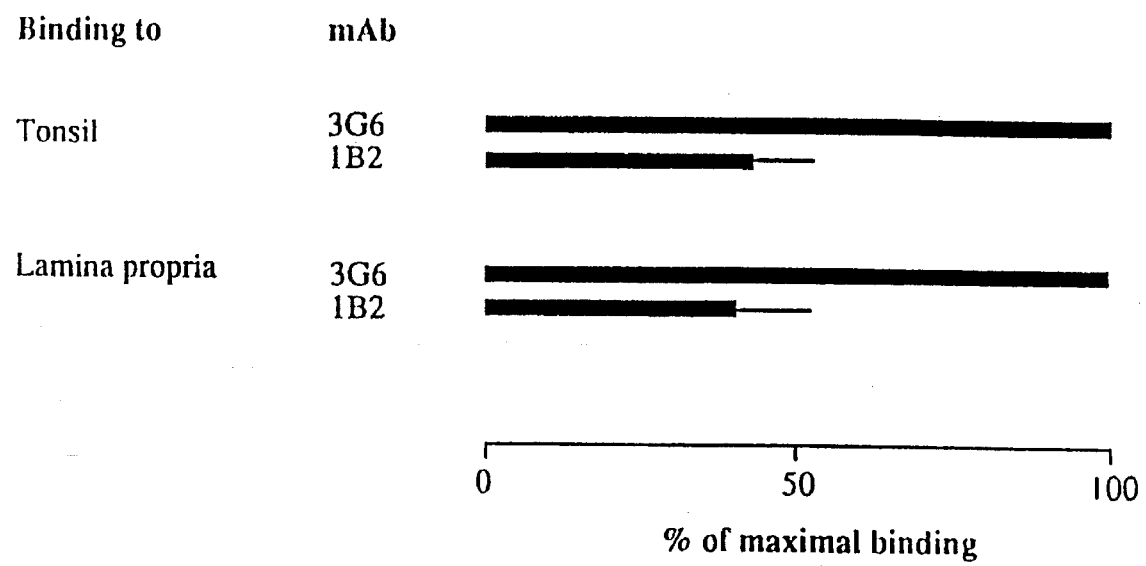
FIG. 7. The inflammation-induced VAP-1 mediates lymphocyte binding. A frozen section binding assay was performed, in which binding of PBL to Factor VIII positive venules in inflamed lamina propria was analyzed. Inhibition assays were done by preincubating tissue sections with mAbs 1B2 and 3G6. Results are presented as percentages of control binding with standard errors (i.e., binding of PBL in the presence of mAb 3G6 defines 100% binding).

In vitro frozen section assays were performed as described in Example 3. Monoclonal antibody 1B2 inhibited lymphocyte binding to small vessels of the lamina propria by approximately 60% (FIG. 7) in two gut samples that abundantly expressed VAP-1.

Example 8

The 170 kD form is the major immunoreactive species of VAP-1 in tonsil

As shown in Example 3, silver-staining of immunoaffinity-purified VAP-1 and immunoprecipitates from surface-iodinated tonsil tissue fragments yielded two-different sized species of VAP-1 molecule. Therefore, in the present example, immunoblotting and metabolic labelling were used to analyze which form of VAP-1 is the mature immunoreactive molecule.

Materials and Methods
Cells and Tissues

Human tonsils were obtained from surgical operations.
Immunoblotting

Proteins from NP-40 lysates of stromal elements of tonsil were concentrated by precipitation with 10% $(NH_4)_2SO_4$ as described (Salmi et al., Science 257:1407–1409 (1992)). Aliquots of the precipitate were mixed with equal volumes of Laemmli's sample buffer with or without reduction (5% 2-ME). Samples were then subjected to gentle heating (20 min 37° C.) or boiling (5 min, 100° C.), and loaded on 5–12.5% SDS-PAGE gels. The resolved proteins were transferred onto nitrocellulose sheets (Hybond-C Super, Amersham Intl., Buckinghamshire, England) by blotting in liquid-based Hoeffer electroblotter using buffers and adjustments similar to those described earlier (Salmi et al., *J. Cell. Biol.* 122:431–442 (1993)). Nitrocellulose strips were then developed according the manufacturer's recommendations using Amersham enhanced chemiluminescence-detection kit for Western blotting. Briefly, blocking was done with PBS containing 10% nonfat milk powder and 0.3% Tween 20 for 1 h, and primary antibodies were used at 2 µg/ml.

Metabolic Labeling

Small tissue cubes were cut from freshly obtained tonsils and subjected to metabolic labeling in an in vitro organ culture. Tissue slices were washed in PBS, transferred to 24 well plates (~100 mg tissue/well), and starved for 60 min in methionine-cysteine free DMEM (Gibco) supplemented with 10% dialyzed FCS, 4 mM L-glutamine, 10 mM Hepes and 1 mM sodium pyruvate. 0.5 mCi/ml $^{35}$S-methionine/$^{35}$S-cysteine (Translabel, ICN Biomedicals Inc., CA) was then added to each well and incubation was continued for 4 h. Thereafter, the tissue fragments were collected, washed and lysed (1 ml lysis buffer containing 150 mM NaCl, 10 mM Tris-base (pH 7.2), 1.5 mM MgCl$_2$ 1% NP-40, and protease inhibitors 1% aprotinin, 1 mM PMSF, 1 mM sodium azide, 10 µg/ml pepstain A and 1 mM EDTA was added per 100 mg tissue) overnight at 4° C. Insoluble material was removed by centrifugation (12 000 g, 30 min, 4° C.). The lysates were then precleared once with 100 µl Protein A SEPHAROSE™ (beaded agarose) beads, and three times with 100 µl aliquots of rabbit anti-mouse Ig derivatized Protein A SEPHAROSE ™ (beaded agarose) beads. For immunoprecipitations, 15 µl Protein A beads to which rabbit anti-mouse Ig had been previously bound were preloaded with 1.5 ml 100 µg/ml of purified 1B2 or negative control mAb overnight at 4° C. Precleared lysates were mixed with specifically coupled Protein A beads and incubated for 4 h at 4° C. with rocking. The beads were washed six times in the washing buffer (100 mM NaCl, 10 mM Na$_2$HPO$_4$, 0.2% sodiumdeoxycholate, 0.01% SDS and 1% NP-40). Antigens were eluted with Laemmli's sample buffer containing 5% 2-ME, and resolved in 5–12.5% SDS-PAGE. After electrophoresis, the gels were fixed, soaked in Enlightning (DuPont, Boston, Mass.) for 30 min, dried and subjected to autoradiography at −70° C.

Results (NH$_4$)$_2$SO$_4$ precipitated NP-40 lysates of tonsil stroma were utilized as a source of VAP-1 antigen. Lysates were mixed with Laemmli's sample buffer (with or without reduction), heated, resolved in SDS-PAGE, electroblotted onto nitrocellulose membranes using a liquid-based system at +4° C., and VAP-1 was visualized using mAb 1B2 and an enhanced chemiluminescence detection system. When reduced or non-reduced samples were boiled (100° C., 5 min) before loading on the gel, no signal was detectable in immunoblotting (FIG. 8A, lanes 1–3). However, when the sample was not reduced and only mildly heated (20 min 37° C.), a specific band at the 170 kD range was seen (FIG. 8A, lane 4). VAP-1 reactivity was destroyed in the gently heated sample by reduction, as shown in lane 6. Thus, in tonsil the 1B2 immunoreactive epitope is in the 170 kD form of the molecule when the analysis is done under conditions that avoid any harsh treatment of the sample.

To analyze further the synthesis of VAP-1 in tonsil, slices of human tonsil were metabolically labeled with $^{35}$S-methionine/$^{35}$S-cysteine in vitro for 4 hours and NP-40 soluble proteins were immunoprecipitated with mAb 1B2. From this material, two mAb 1B2 specific bands were detected (FIG. 8B). The size of the more prominent band at 170 kD was similar to the mAb 1B2 reactive band seen in immunoblotting, and thus represents the intact VAP-1 molecule. A less abundant 90 kD species was also specifically immunoprecipitated with mAb 1B2. These data indicate that both the 170 and 90 kD forms of VAP-1 are actively produced in human lymphatic tissues.

Discussion

Both the 170 and 90 kD forms of VAP-1 are produced in lymphoid tissue. The 170 kD form of VAP-1 is identical with the about 180–200 kD form described in Example 3. In Example 3, immunoaffinity-isolates of 1B2-reactive material from tonsil lysates and immunoprecipitates from small fragments of tonsil stroma subjected to peroxidase-catalyzed surface labeling with $^{125}$I were analyzed. The small difference in apparent size is due to differences in gel systems (linear vs. gradient) and in sample treatment.

Example 9

VAP-1 is a sialylated glycoprotein in tonsil vessels

Since the function of most adhesion molecules is critically dependent on posttranslational modifications, a more thorough understanding of the structure of VAP-1 was desirable. Therefore, we took advantage of the immunoblotting assay described in Example 8 to assess the potential oligosaccharide modifications of VAP-1.

Materials and Methods

Cells and Tissues

Human tonsils were obtained from surgical operations.

Sialidase, O-glycanase and N-glycanase treatments

Tonsils were lysed in 20 mM sodium phosphate buffer, pH 6.0 containing 1% NP-40. After removing insoluble material by centrifugation, the supernatant was depleted of immunoglobulins by incubation with Protein G beads (Pharmacia) for 2 h at 4° C., and then discarding the beads. For sialidase treatment, 25 mU *Vibrio cholerae* neuraminidase (Behringwerke AG, Marburg) was added to 150 µl lysate for 2 h at 37°. Thereafter, half of the lysate was subjected to further digestion with 16 mU of recombinant endo-α-N-acetylgalactosaminidase (O-glycanase, Genzyme, Cambridge, Mass.) overnight at 37° C. To treat the lysate with N-glycanase, 0.5% SDS, 5 mM EDTA and 1.2 U peptide:N-glycosidase F (Genzyme) was added to an aliquot of precleared sample overnight at 37° C. Finally, the digested samples were mixed with non-reduced Laemmli's sample buffer, separated in SDS-PAGE, and immunoblotted as described above in Example 8.

VAP-1 antigen was affinity-isolated from $^{35}$S-methionine$^{35}$S-cysteine labeled tonsil tissue fragments as described above. Thereafter, the affinity matrix was washed 6 times with the washing buffer and additionally twice with PBS. For removing sialic acids, VAP-1 immunocomplexes were treated with 0.1 U neuraminidase from *Vibrio cholerae* (Calbiochem, San Diego, Calif.) at 37° C. for 4 h. The enzyme was removed by washing twice in PBS and the beads were resuspended in Laemmli's sample buffer containing 5% 2-ME or in 100 µl PBS. To the latter tube, 4 mU O-glycanase was added, and the incubation was continued overnight at 37° C. For removing N-linked oligosaccharides, VAP-1 antigen was released from the 1B2-Protein A SEPHAROSE™ (beaded agarose) by boiling for 5 min in 30 µl endo F buffer (100 mM Tris-HCl, pH 8.8, 10 mM EDTA, 0.5% SDS, 1% 2-ME). The supernatant was transferred to a new tube into which 5 µl 10% NP-40 and 0.3 U N-glycanase was added. Digestion was allowed to proceed overnight at 37° C. Samples from sialidase, O- and N-glycanase treatments were subjected to gel electrophoresis and enhancing as described above.

Results

Figure 9B:
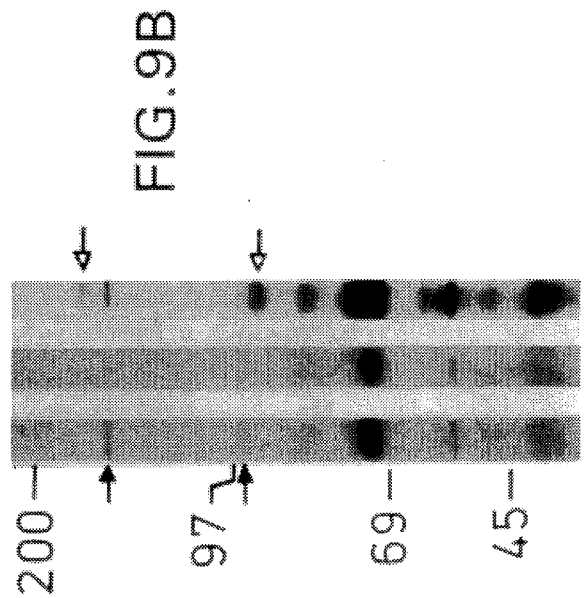
FIG. 9 (A–B). VAP-1 is a sialoglycoprotein in tonsil. (A) Tonsil lysates were subjected to no treatment, digestion with sialidase, sialidase follow by O-glycanase and N-glycanase before SDS-PAGE and immunoblotting with mAb 1B2 or negative control. (B) VAP-1 isolated from $^{35}$S-cysteine/$^{35}$S-methionine labeled tonsil pieces was either treated with sialidase and O-glycanase or left untreated. Black arrows point to the original 170 and 90 kD forms, and white arrows to the 180 and 85 kD forms detected after enzymatic treatment. Note that three times more digested material than untreated ones was loaded.
Figure 9A:
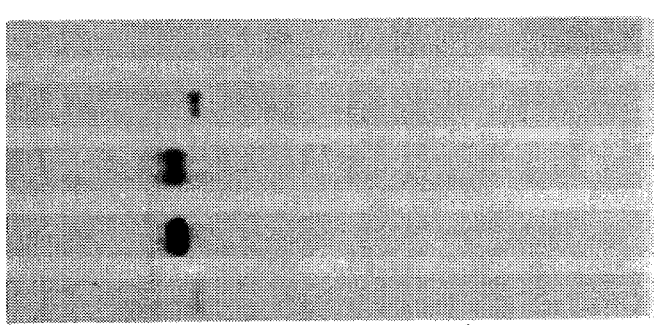

Tonsil lysate was depleted of immunoglobulins with Protein G-beads, and subjected to different glycosidase digestions prior to gel electrophoresis and immunoblotting (FIG. 9A). Neuraminidase treatment that removes sialic acids from the oligosaccharide side chains increased the apparent molecular weight of VAP-1 antigen. This kind of paradoxical change in the electrophoretic mobility after sialidase treatment is consistent with a reduction in the net charge of the molecule due to the removal of negatively charged sialic acid residues. Enzymatic digestion of sialidase treated sample with O-glycanase had only marginal effect on the size of VAP-1, whereas N-glycanase treatment did not affect the mobility of VAP-1 antigen. The enzymatic activities of sialidase, O- and N-glycanase were confirmed in parallel immunoblottings in which the expected reduction in mass was observed with CD44 that is known to be modified with these sugars (Jalkanen et al., *J. Cell Biol.* 105:983–90 (1987)). These results indicate that VAP-1 is a sialoglycoprotein in tonsil and mAb 1B2 detects a protein rather than a sugar epitope.

To confirm the immunoblotting results, VAP-1 was affinity isolated from metabolically labeled tonsil fragments and treated with glycosidases. Again, neuraminidase treatment increased the size of VAP-1 (FIG. 9B). However, only a fraction of 170 kD VAP-1 displayed altered electrophoretic mobility indicating that during a 4 h pulse sialylation of all labeled VAP-1 molecules was not completed. Interestingly, the 90 kD form of VAP-1 also contained sialic acids, since its size was reduced after neuraminidase treatment.

Discussion

VAP-1 is a sialylated glycoprotein in tonsil. In both metabolic labeling and in immunoblotting experiments, neuraminidase treatment increased the molecular weight of VAP-1. Since Vibrio cholerae neuraminidase was used, the present data indicate that sialic acids in VAP-1 are in terminal position and linked by one of the common glycosidic linkages ($\alpha 2,3$, $\alpha 2,6$ or $\alpha 2,8$) to the oligosaccharide core. The sialic acids appear to be presented on a short O-linked oligosaccharide core, since only a very minor shift in electrophoretic mobility was seen after O-glycanase treatment, and no evidence of N-linked glycans was seen. Alternatively, the underlying glycan core may be resistant to the enzymes used.

Example 10

Sialic acid modifications of VAP-1 are essential for lymphocyte binding

We studied whether the sialic acid decorations of VAP-1 are necessary for its adhesive function.

Materials and Methods

Cells and Tissues

Human tonsils were obtained from surgical operations. PBL were isolated from healthy adult volunteers using Ficoll gradient centrifugation.

Immunoperoxidase stainings

Immunoperoxidase stainings of acetone-fixed frozen sections were done as described in Example 1. Neuraminidase treatment of frozen sections was performed by incubating the sections with 5 mU neuraminidase (Behringwerke) in 50 mM sodium acetate buffer, pH 5.5 with 154 mM NaCl and 9 mM $CaCl_2$ for 30 min in a humidified chamber at 37° C. Control sections were treated with the buffer only. After digestions, the enzyme was washed away, and the sections stained normally.

HEV-binding assay

The in vitro frozen section assay was conducted as described earlier (Jalkanen et al., *Blood* 66:577–582 (1985)). In brief, 8 μm frozen sections from tonsil were preincubated with mAbs (100 μg/ml diluted in RPMI 1640 containing 10% FCS and 10 mM Hepes) for 30 min at 4° C. under constant rotation on an orbital shaker (60 rpm). Thereafter, $3 \times 10^6$ PBL in the same medium were added onto tissue sections and incubation continued for another 30 min under rotation. The non-adherent cells were gently tilted off, and the adherent cells were fixed in 1% glutaraldehyde. PBL binding to HEV was counted from coded samples under dark-field illumination. At least 120 HEV per sample were counted. The number of cells adherent to HEV in the presence of the negative control defines 100% adherence.

For analyzing the role of sialic acids of VAP-1 in lymphocyte binding to HEV, target tissue was treated with neuraminidase as described above. After washings, the sections were then preincubated with mAbs, and finally PBL were added as in standard HEV assays. Control sections were incubated with the sialidase buffer in the first step.

Results

Initially, frozen sections of tonsils were treated with neuraminidase, and thereafter immunoperoxidase staining was performed. Consistent with the biochemical data, mAb 1B2 epitope remained intact after removing sialic acids from the section (data not shown). Effectiveness of sialic acid removal was confirmed in stainings in which all mAb CSLEX-1 (against sialyl Lewis x) reactivity disappeared after the neuraminidase digestion, but not in the sections incubated with the buffer only.

Figure 10:
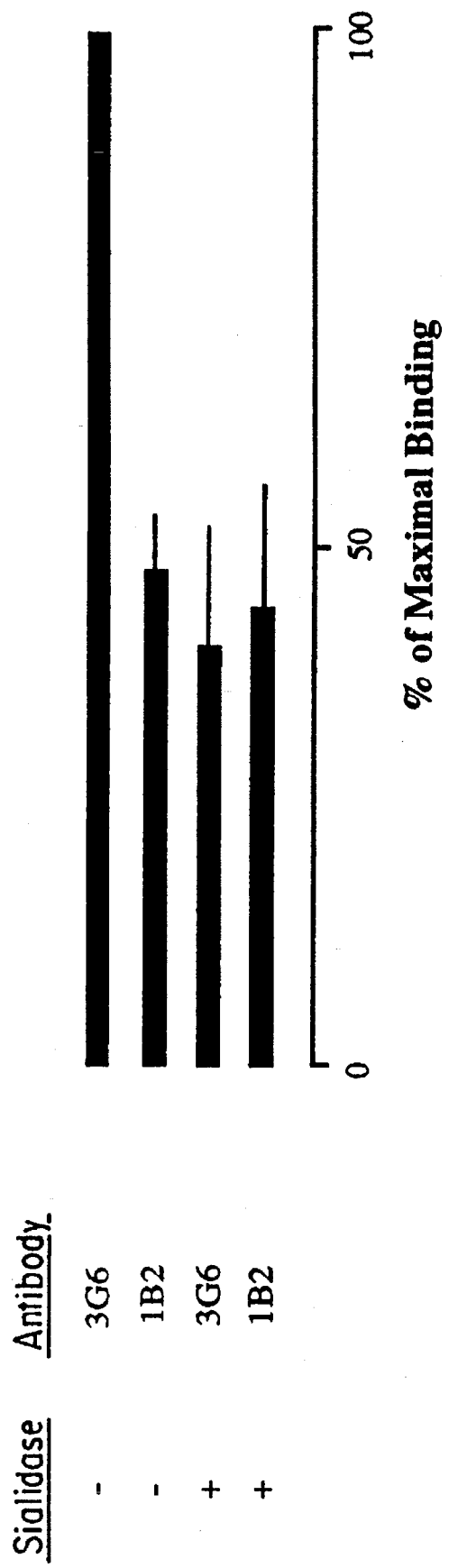
FIG. 10. Sialic acids in VAP-1 are a prerequisite for lymphocyte binding. Tonsil sections were treated with sialidase, or buffer alone, preincubated with the indicated mAbs, and thereafter binding of PBL to HEV was analyzed. Results are mean ±SEM of two independent experiments (different tonsils and PBL). Results are expressed as percentage of maximal binding (binding in the presence of the negative control mAb (3G6) defines 100% binding).

To analyze the importance of sialic acid decorations of VAP-1 in mediating lymphocyte binding, an in vitro frozen section assay was employed (FIG. 10). Tonsil sections were treated with neuraminidase, or buffer only, washed, and then incubated with mAb 1B2 or a negative control mAb, and finally lymphocytes were applied onto the sections. MAb 1B2 abrogated approximately 50% of lymphocyte binding to tonsil HEV in the buffer treated control samples. When the target tissue was pretreated with neuraminidase, lymphocyte binding was reduced by 60% when compared to buffer controls. Strikingly, after neuraminidase treatment, mAb 1B2 had no inhibitory effect on lymphocyte binding to tonsil HEV. These data show that removal of sialic acids dramatically alters the capacity of tonsil venules to bind lymphocytes. Specifically, desialylated form of VAP-1 can no longer mediate lymphocyte binding, although it is still recognized by mAb 1B2.

Discussion

Function of VAP-1 is critically dependent on the proper sialylation. This was shown in HEV-assays, in which removal of sialic acids from VAP-1 completely abolished its capacity to mediate lymphocyte binding to tonsil vessels. However, since inhibitory mAbs 1B2 and 5B11 are not against sugar epitopes, a conformation-dependent protein epitope exposed only in the mature form of VAP-1 is also required for binding. Thus, it can be envisioned that the true binding site is composed of a pocket containing residues from both protein core and sialic acids. In mouse, sialidase treatment has been shown to reduce lymphocyte binding to peripheral lymph nodes by 90%, to mesenteric nodes by 50% and to have no effect on binding to mucosal HEV (Rosen et al., *Science* 228:1005–1007 (1985)). Since tonsil represents an organ with dual endothelial recognition specificities (peripheral and mucosal) our results extend the earlier observations of the critical importance of sialic acids in lymphocyte binding to human system. Moreover, we show directly that VAP-1 is a principal neuraminidase sensitive adhesion molecule that mediates lymphocyte binding to peripheral lymph node type venules under non-static conditions. These data suggest that VAP-1 may operate in the first step of leukocyte-endothelial cell interaction where lymphocytes make initial contacts with endothelial lining under flow conditions (Butcher et al., Cell 67:1033–1036 (1991)). Notably, other endothelial molecules (GlyCAM-1, CD34) involved in this step are mucin-like glycoproteins with abundant sialic acid decorations (Lasky et al., Cell 69:927–938 (1992), Baumhueter et al., Science 262:436–438 (1993)). Hence, the biochemical structure and function of VAP-1 strongly suggests that it presents an alternative endothelial cell ligand for initial lymphocyte binding, thus increasing the possibilities for regulating the diversity and specificity of lymphocyte-endothelial cell interaction.

Example 11

VAP-1 lacks common-type oligosaccharide modifications in HEC

Since a cell line model would be feasible for detailed biochemical studies, we searched for a VAP-1 positive endothelial cell line. In particular, two cultured endothelial cells, human umbilical vein endothelial cells (HUVEC) and an endothelial cell hybrid (HEC), were studied for expression of VAP-1.
Materials and Methods
Cells and Tissues HEC line, a derivative of EaHy-926 endothelial cell hybrid (Edgell et at., Proc. Natl. Acad. Sci. USA 80:3734–3737 (1983)) that retains several phenotypic and functional properties of normal endothelial cells, was maintained as described (Salmi et al., J. Exp. Med. 178:2255–2260 (1993b)). HUVEC were collected as described earlier (Airas et al., J. Immunol. 151:4228–4238 (1993)).
Immunofluorescence stainings HEC grown on 8 well plastic slides (LabTek chamber slides, Nunc) were stained using a protocol described earlier (Salmi et al., J. Cell. Biol. 122:431–442 (1993)). Briefly, the cells were fixed in 1% formalin and permeabilized by acetone. Primary antibodies were added at 20 µg/ml (diluted in PBS containing 1% FCS and 1 mM sodium azide), and FITC-conjugated sheep anti-mouse Ig along with 5% human AB-serum was used as a second-stage reagent. Thereafter, cells were mounted in 50% glycerol, 2×PBS, 0.1% sodium azide and 100 µg/ml DABCO (1,4-diazabicyclo(2,2,2)octane, Sigma).
Metabolic Labeling and Pulse Chase Experiments Metabolic labeling of HEC with $^{35}$S-methionine/$^{35}$S-cysteine was done as described in Example 8 with the following modifications. Subconfluent monolayers in 75 cm$^2$ tissue culture flasks were rinsed twice with PBS before 45 min starvation. Labelling time was 3 h, and thereafter cells were washed four times with cold PBS. One ml lysis buffer was added to each flask, and after a minimum of 2 hours at 4° C. cells were harvested by scraping. Preclearing was done three times with 50 µl rabbit anti-mouse Protein A. Immunoprecipitated antigen from cells of one 75 cm$^2$ bottle were used per lane. In separate experiments the same lysis buffer without EDTA was shown to yield identical results indicating that divalent cation chelation did not affect the immunoprecipitation results.

Labeling with $^{35}$S-sulphate was done similarly, except that starvation was done in sulphate-free DMEM, overnight incubation with 2.5 mCi H$_2$$^{35}$SO$_4$ was used, only two rounds of Protein A preclearing were performed, and after immunoprecipitations the beads were washed only 4 times before eluting the antigens.

Figure 11A:
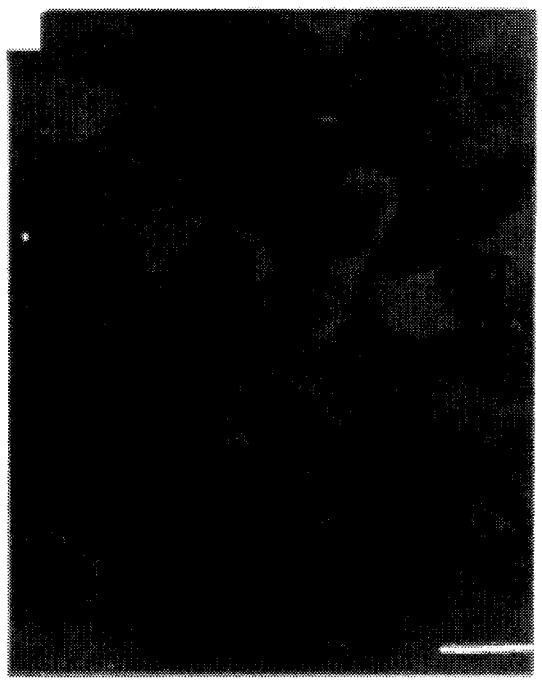
FIG. 11 (A–B). VAP-1 is present intracellularly in HEC. HEC were fixed with 1% formaline and permeabilized with acetone and thereafter stained for immunofluorescence with (A) mAb 1B2 and (B) mAb 3G6, a negative control. VAP-1 is distributed throughout the cytoplasm. Note that the nuclei are VAP-1 negative, whereas most autofluorescence comes from the nuclei in the negative control. Due to the low intensity of VAP-1 expression in HEC, the staining comprised of two rounds of incubation with the primary and secondary antibodies. Bar=10 µm.
Figure 11B:
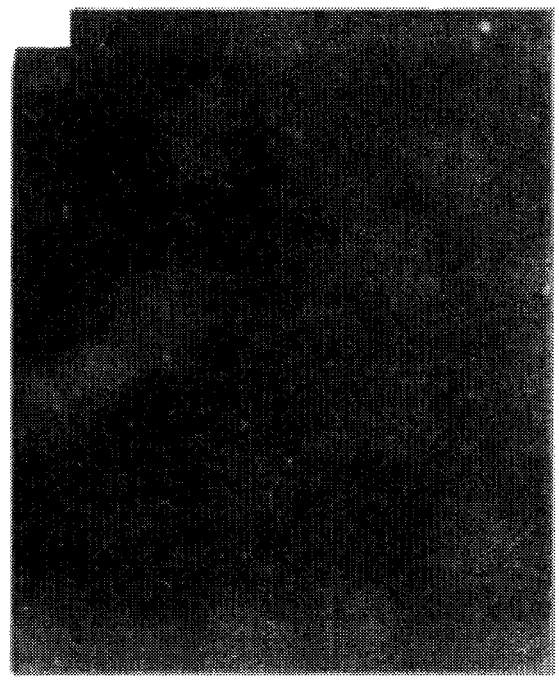

For biosynthetic studies of VAP-1, starved HEC were pulsed with $^{35}$S-methionine/$^{35}$S-cysteine for 5, 15 or 30 min, and then chased for 0, 15, 30, 120 min or overnight in the HEC medium supplemented with 10×methionine (0.15 mg/ml) and 10×cysteine (0.5 mg/ml). After the chase period, bottles were transferred onto ice, rinsed and the cells were processed as described above.
Sialidase, O-glycanase, N-glycanase, tunicamycin and benzyl-N-acetylgalactosaminide treatments HEC were metabolically labeled with $^{35}$S-methionine/$^{35}$S-cysteine for 30 min and chased overnight. Thereafter, affinity-isolated VAP-1 was subject to sialidase, O- and N-glycanase treatments exactly as described in Example 9 above for tonsil VAP-1. To treat HEC with tunicamycin, HEC were starved in methionine/cysteine free DMEM to which 0 µg/ml, 1 µg/ml, or 10 µg/ml tunicamycin (Sigma) was added. After one hour, the radioactive label was added and incubation continued for further 3 hours. To inhibit synthesis of O-linked oligosaccharides, cells were treated overnight with 0 mM, 2 mM or 10 mM benzyl-N-acetylgalactosaminide (Sigma). Thereafter, 1 h starvation and 3 h labeling were done in the presence of the same concentrations of benzyl-N-acetylgalactosaminide. After labelings, lysis, immunoprecipitations and electrophoresis were performed as described in Example 9.
Results VAP-1 is absent from the surface of resting and activated human umbilical vein endothelial cells (HUVEC) and an endothelial cell hybrid HEC (Salmi et al., Science 257:1407–1409 (1992); Salmi et at., J. Exp. Med. 178:2255–2260 (1993)). However, when studied for intracellular expression of VAP-1, HUVEC and HEC displayed faint but definitive staining with mAb 1B2 after fixation and permeabilization (FIG. 11). VAP-1 antigen was localized in minute discrete granules throughout the whole cytoplasm, and was absent from the nuclei.

To determine the molecular mass of VAP-1 in HEC, the cells were metabolically labeled with inorganic $^{35}$—SO$_4$, since several macromolecules in endothelial cells are known to incorporate this molecule well (Andrews et at., J. Cell Sci. 57:277–292 (1982)). However, as shown in FIG. 12A no signal was observed after precipitation with mAb 1B2, although a strong signal was detected from mAb Hermes-3 control precipitations (Hermes-3 detects CD44 that is known to incorporate sulphate well, Jalkanen et al., J. Cell Biol. 105:983–90 (1987). Next, $^{35}$S-methionine/$^{35}$S-cysteine was used as a label. Under non-reducing conditions, a somewhat diffuse 180 kD band was seen (FIG. 12B, lane 1). Under reducing conditions (5% 2-ME), the electrophoretic mobility of VAP-1 antigen was not shifted although the band was sharper (FIG. 12B, lane 4). In HEC, no 90 kD form of VAP-1 was detectable.

To study whether VAP-1 in cultured endothelial cells carries the appropriate posttranslational modifications, the effect of glycosidase treatment on the molecular mass of VAP-1 was analyzed. Interestingly, neuraminidase treatment had no effect on the electrophoretic mobility of VAP-1 antigen in HEC (FIG. 12B, lane 5). VAP-1 in HEC also lacked all detectable O-linked glycans, since neither digestion with O-glycanase nor labeling HEC in the presence of benzyl-N-acetylgalactosaminide, a metabolic inhibitor of O-linked oligosaccharide synthesis (Kuan et al., *J. Biol. Chem.* 264:19271–19277 (1989)), altered the size of VAP-1 antigen (FIG. 12B and C). Treatment of VAP-1 antigen with N-glycanase or labeling of cells in the presence of tunicamycin failed to identify any N-linked oligosaccharides in VAP-1 (FIG. 12B and C). The enzymatic activities and efficacy of treatments with metabolic inhibitors were confirmed in parallel immunoprecipitations in which the expected reduction in mass was observed in CD44. Thus, these experiments strongly suggest that in HEC VAP-1 lacks sialic acids, O-linked and N-linked oligosaccharides.

Figure 13:
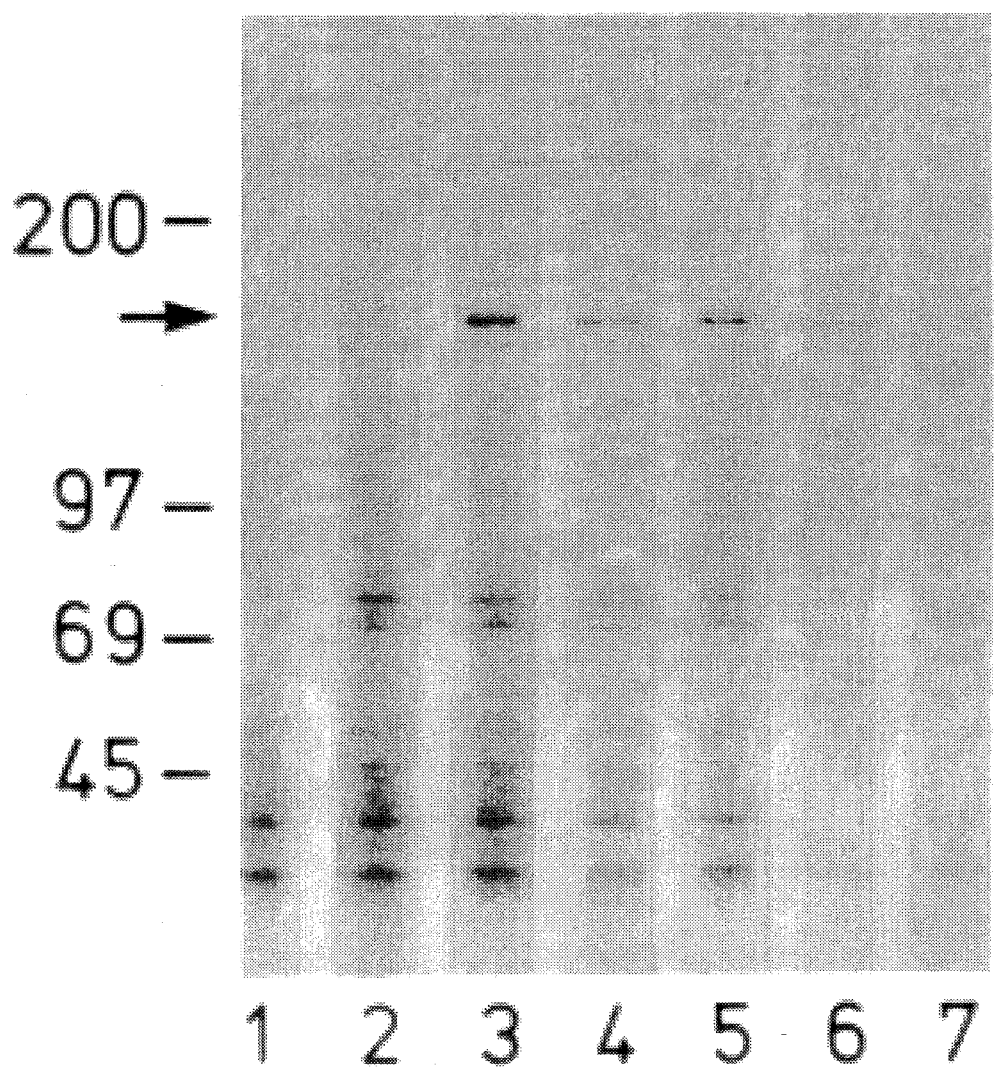
FIG. 13. VAP-1 lacks detectable precursor forms in HEC. HEC were pulsed for 5 min with $^{35}$S-methionine/$^{35}$S-cysteine and chased for the indicated periods (0 min, 15 min, 30 min, 120 min and 18 h). At each time point, cells were lysed and 1B2 and control (3G6) immunoprecipitations were performed. The arrow indicates the specific 1B2 immunoprecipitate.

Biosynthetic studies were undertaken to see whether VAP-1 has any recognizable precursor forms in HEC. In pulse-chase experiments (with 30, 15, or 5 min pulse and 0, 15, 30, 120 min and 18 h chase) no precursor forms were detectable (FIG. 13). These data indicate that in HEC the 180 kD form of VAP-1 recognized by mAb 1B2 is minimally, if at all, subjected to post translational modifications. Together, the biochemical analysis of VAP-1 in HEC indicate that this cell line is not capable of modifying VAP-1 with appropriate oligosaccharides, which may be the reason for the solely intracytoplasmic localization of VAP-1 in HEC.

Discussion

Biochemical analysis of VAP-1 in HEC revealed major endothelial cell-type specific differences in glycosylation. Lack of sialic acids, O- and N-linked glycans in VAP-1 in HEC was strongly indicated by inefficiency of sialidase, O-glycanase, benzyl-N-acetylgalactosaminide, N-glycanase and tunicamycin treatments. Also, when the biosynthesis of VAP-1 was analyzed using pulse-chase experiments, we were unable to detect any recognizable protein precursors. Together, these data indicate that the 180 kD form of VAP-1 in HEC is not posttranslationally modified by most typical oligosaccharide side chains, and may thus be the equivalent of the desialylated 180 kD form of VAP-1 in tonsil. In HEC, VAP-1 is present in the cytoplasm and not on the cell surface, whereas in tonsil HEV VAP-1 is both lumenal and in discrete cytoplasmic granules. The lack of surface expression of VAP-1 in HEC may be due to the defective sialylation of VAP-1. The distinct oligosaccharide modifications of VAP-1 in an endothelial cell line and in vivo situation again underscore the potential risks of using cell lines as the sole model for studying the function of endothelial adhesion molecules.

Example 12

New monoclonal antibodies raised against the 170 kD and 90 kD 1B2 immunoprecipitable proteins To study the relationship between the two forms of VAP-1 in more detail, mAbs against both proteins were raised.

Materials and Methods

Antibodies

MAb 1B2 is an inhibitory antibody (mouse IgG1) against VAP-1 (Salmi et al., *Science* 257:1407–1409 (1992)). MAb SP-2 is against Mac-2-BP. FITC-conjugated sheep anti-mouse Ig was from Sigma (St. Louis, Mo.), rabbit anti-mouse Ig and peroxidase-conjugated goat anti-mouse Ig were from Dakopatt (Glostrup, Denmark) and an EIA grade peroxidase-conjugated goat anti-mouse (used in ECL) was from Bio-Rad Labs (Hercules, Calif.) Hermes-3 against CD44 was produced as described (Jalkanen et al., *J. Cell Biol.* 105:983–90 (1987)), and 3G6, a mouse IgG1 against chicken T cells, was used as a negative control.

A new mAb was produced against the 170 kD form of VAP-1. VAP-1 was immunoaffinity-purified from ammonium sulphate precipitates of NP-40 lysates of tonsil stroma using mAb 1B2 coupled to CnBr-activated SEPHAROSE™-4B (beaded agarose) beads as described earlier (Salmi et al., *Science* 257:1407–1409 (1992)). The antigen was resolved in 5–12.5% SDS-PAGE under reducing conditions. The 170 kD band was excised from the silver stained gel after drying, minced into small pieces, immersed in incomplete Freund's adjuvant, and injected into footpads of specific pathogen free Balb/C mice three times at one week's intervals. Popliteal lymph node lymphocytes were fused with NS-1 myeloma cells, and the hybridoma supernatants were tested using immunoperoxidase staining of tonsil sections. After subcloning, one of the mAbs (3B11) was selected for further studies.

MAbs against the amino acids 8–17 of the N-terminus of the 90 kD 1B2 immunoprecipitable material (Salmi et al., *Science* 257:1407–1409 (1992)) were raised using the same methodology as we have employed earlier for producing other anti-peptide mAbs (Salmi et al., *J. Cell. Biol.* 122:431–442 (1993)). Briefly, approximately 50 µg HPLC purified decamer peptide (LVNGASANEG) [SEQ.ID.NO.1] in incomplete Freund's adjuvant was used to immunize mice as described above for the 170 kD band. Hybridomas were tested in immunostaining of tonsil, in peptide EIA and in a dot blot assay. Peptide EIA was performed similarly as described earlier for analysis of other anti-peptide mAbs (Salmi et al., *J. Cell. Biol.* 122:431–442 (1993)). In dot blot assay, 10 µg peptide (the immunogen and an unrelated synthetic peptide) were transferred onto nitrocellulose filters using a Convertible dot blot apparatus, and detected as described below for immunoblotting. On the basis of tissue staining and positive reactivity in dot blot assay, a mAb (5B11) was selected and subcloned for further studies. A polyclonal antibody against the same synthetic N-terminal peptide from the 90 kD protein was made by immunizing mice intraperitoneally with the peptide in complete Freund's adjuvant. Mice were boosted at one week intervals for eight times with the peptide in incomplete Freund's adjuvant and a final boost in PBS was given three days before collecting the serum.

Immunoblotting

Immunoblotting was performed as described in Example 8.

Immunoperoxidase stainings

Immunoperoxidase staining was performed as described in Example 1.

HEV-binding assay

The HEV-binding assay was performed as described in Example 10.

Results

Figure 14A:
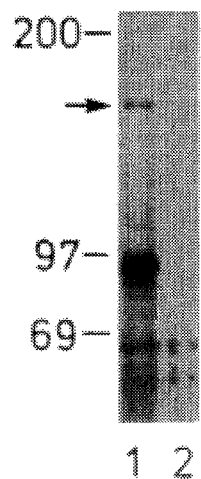
FIG. 14 (A–C). mAb 3B11 is against the 170 kD form of VAP-1. (A) VAP-1 was affinity-isolated from tonsil lysates with mAb 1B2 and visualized by silver staining after separation in SDS-PAGE. Both the 90 kD form and the larger 170 kD form (arrow) are detectable (lane 1). Only sample buffer has been loaded in lane 2 showing the "mercaptan artifact" at ~70 kD and ~50 kD that is commonly observed in silver staining (Dunbar et al., *Meth. Enzymol.* 182:441 (1990)). Immunization with the excised 170 kD band yielded mAb 3B11. (B) MAbs 3B11 and 1B2 stain the same vessels in serial sections (5 µm) in tonsil. MAb 3B11 staining is lumenal in nature, and to assist the comparison, five arrows pointing to corresponding vessels in each micrograph have been included. The vessel shown by the filled arrow shows limited expression of the 3B11 epitope only in the upper part, whereas it is continuously mAb 1B2 positive. Bar=50 µm. (C) In immunoblotting of tonsil lysates mAb 3B11 recognizes a ~170 kD smear under non-reducing conditions. Immunodetection was done with mAb 3B11 (lane 1), 1B2 (lane 2) and 3G6 (lane 3).
Figure 14C:
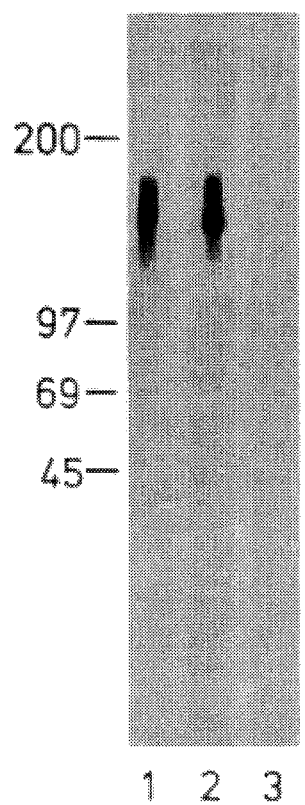
Figure 14B:
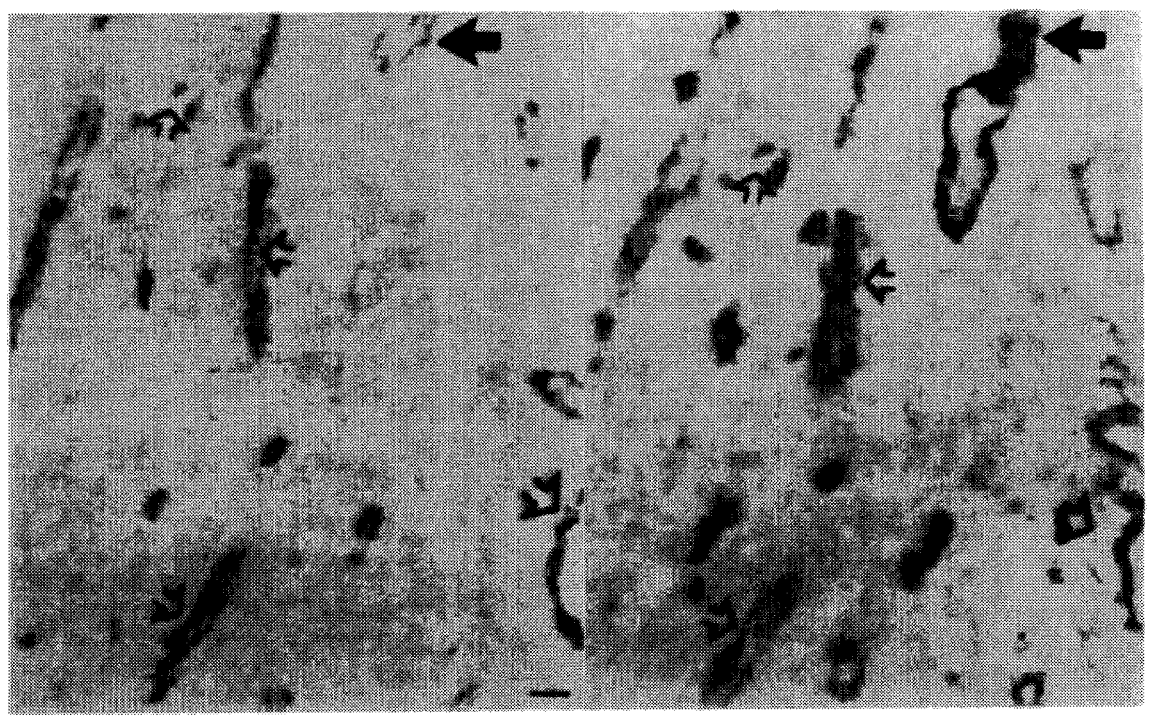

New mAbs against the larger form of VAP-1 (170 kD) were produced by immunizing mice with the 170 kD protein band excised from a silver stained gel, in which 1B2 immunoaffinity-purified material from tonsil had been separated (FIG. 14A). A mAb 3B11 thus obtained, stained HEV and dendritic-like cells in tonsil. The staining patterns of mAbs 1B2 and 3B11 seemed very similar and to verify the co-localization, serial sections were evaluated. It was evident that these two mAbs stained the same vessels and dendritic cells of germinal centers (FIG. 14B), although occasional 3B11-negative 1B2-positive vessels were detected. MAb 3B11 staining appeared to concentrate to the lumenal side of endothelial cells, and it was distinctively granular. Like the 1B2 epitope, the 3B11 epitope was absent from fibroblasts, lymphoid and epithelial cells but, in contrast to mAb 1B2, also from the smooth muscle layer of larger vessels and bowel wall (Table 2). These data indicate that VAP-1 in muscle cells differs from that in endothelial cells and dendritic cells. In immunoblotting, mAb 3B11 recognized the expected ~170 kD molecule in tonsil (FIG. 14C, lane 1). The functional role of the 3B11 epitope was analyzed in the frozen section binding assay. In concordance with our earlier results, mAb 1B2 inhibited binding of PBL to tonsil HEV by ~50%. In contrast, only marginal, if any, interference with PBL adherence to HEV in the presence of mAb 3B11 was observed (FIG. 15), indicating that it is against a non-functional epitope of VAP-1.

Figures 16A, 16C:
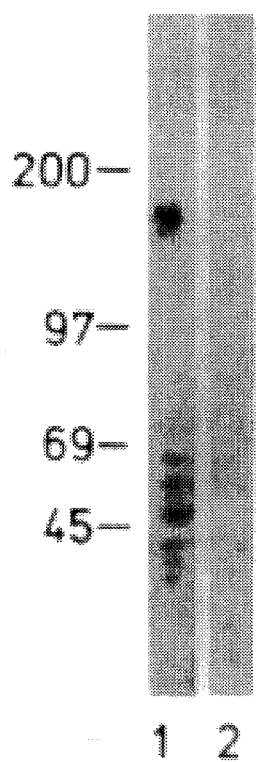
FIG. 16 (A–C). MAb 5B11 recognizes the 170 kD form of VAP-1. (A) The N-terminal amino acid sequence of the 90 kD mAb 1B2 precipitable protein. The synthetic peptide used for immunization was from the boxed area. (B) MAbs 5B11 and 1B2 stain the same cells in serial sections (5 µm) in tonsil. Arrows point to vessels. gc=germinal center. Bar= 50 µm. (C) MAb 5B11 recognizes the 170 kD form of VAP-1 in immunoblotting. Stromal lysates of tonsil were boiled and separated under non-reducing conditions in SDS-PAGE and immunoblotted with mAb 5B11 (lane 1) and a negative control (3G6, lane 2). The smaller bands in 30–70 kD range react also with the negative control (albeit less intensely).
Figure 16B:

Next, antibodies against a synthetic peptide from the N-terminus of the 1B2 immunopurified 90 kD material were prepared (FIG. 16A). An anti-peptide mAb 5B11 recognized the peptide used in immunization in dot blot assays (mAb 5B11 gave 2.35±0.39 times stronger signal (density) with the immunogen than with a control peptide when measured by an image analyzer). MAb 5B11 reacted with the same cell types as mAb 1B2 in tonsil, and also in serial sections, the two mAbs revealed an identical staining pattern. The intensity of 5B11 staining in germinal center cells was similar to that of mAb 1B2, whereas mAb 5B 11 staining intensity of vessels was always inferior to that of 1B2 (FIG. 16B). Notably, smooth muscle cells were clearly positive with 5B11 (Table 2). Polyclonal serum against the same peptide was raised using an independent immunization protocol and it stained the same structures as mAb 5B11 (data not shown).

Figure 15:
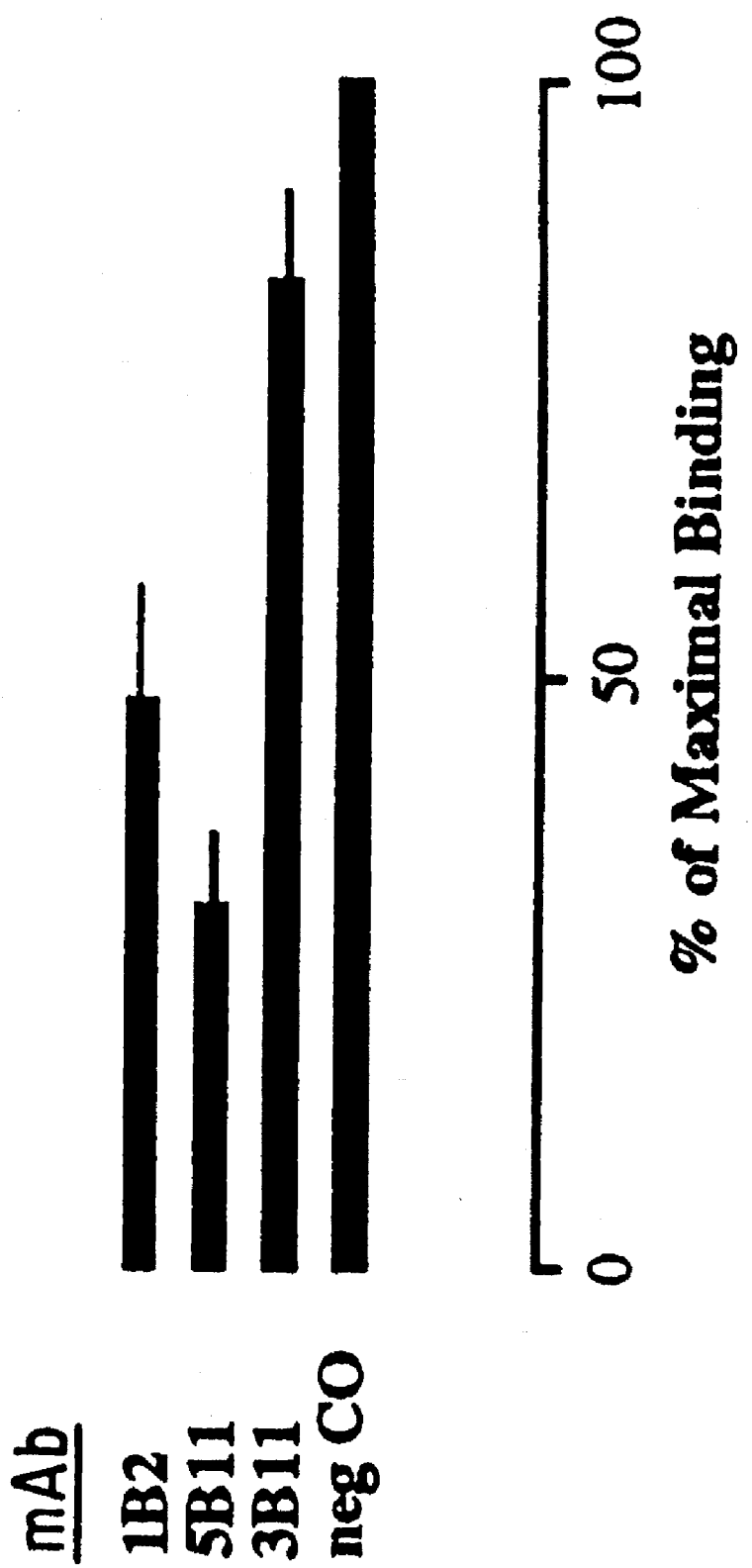
FIG. 15. MAb 5B11 inhibits lymphocyte binding to tonsil HEV. Tonsil sections were pretreated with the mAbs indicated, and PBL were then applied to sections under constant rotation. After 30 min the nonadherent cells were tilted off, adherent PBL were fixed, and PBL bound to HEV were counted. Results are the mean ±SD of three independent experiments. Results are expressed as percentage of maximal binding (binding in the presence of the negative control mAb (3G6) defines 100% binding).

Interestingly, mAb 5B11 specifically recognized the 170 kD form of VAP, but not the 90 kD form, in immunoblotting of tonsil lysates (FIG. 16C). Thus, the same epitope or conformationally similar epitopes exists in the 90 kD molecule and in the larger form of VAP-1. When the function of the 5B11 epitope was studied in HEV assays, mAb 5B11 consistently abrogated about 70% of PBL binding to tonsil HEV (FIG. 15). The inhibition was seen in three independent assays using lymphocytes from three and target tissue from four separate individuals.

TABLE 2

Comparison of three mAbs against VAP-1.

| mAb Immunogen | 1B2 synovial stroma | 3B11 170 kD band | 5B11 90 kD N-terminus |
|---|---|---|---|
| Expression‡ | | | |
| tonsil | | | |
| HEV | +++ | +++ | + |
| lymphocytes | − | − | − |
| dendritic cells | ++ | ++ | ++ |
| fibroblasts | − | − | − |
| epithelial cells | − | − | − |
| appendix | | | |
| HEV | + | + | + |
| lymphocytes | − | − | − |
| smooth muscle | ++ | − | ++ |
| Inhibitory§ | yes | no | yes |

‡ Expression was analyzed from immunoperoxidase stained frozen sections. Intensity of staining was scored as follows: +++, strong; ++ moderate; + weak; −, negative.
§ Blocking PBL binding to HEV in an in vitro frozen section assay.

Discussion

MAb 3B11 was raised against the 170 kD VAP-1 band excised from a silver stained gel. The staining patterns of 1B2 and 3B11 were very similar. In immunoblotting, like 1B2, 3B11 specifically recognized the expected ~170 kD molecule. However, in contrast to 1B2, 3B11 only marginally interfered with PBL adherence to HEV. This indicates that 3B11 is against a non-functional epitope of VAP-1.

MAb 5B11 was raised against the purified decamer peptide (LVNGASANEG) [SEQ.ID.NO.1] of the mouse cyclophilin C associated protein (mCyCAP). As shown in Example 13 below, there is mimotypic identity between VAP-1 and mCyCAP. MAb 5B11 reacted with the same cell types as 1B2 in tonsil. Moreover, the intensity of 5B11 staining in germinal center cells was similar to that of mAb 1B2 and smooth muscle cells were clearly positive with 5B 11. However, 5B 11 staining intensity of vessels was always inferior to that of 1B2. Interestingly, 5B11 consistently abrogated about 70% of PBL binding to tonsil HEV and specifically recognized the 170 kD form of VAP. However, 5B11 did not recognize the 90 kD form in immunoblotting of tonsil lysates.

These data indicate that the 5B11 epitope is involved in lymphocyte-endothelial cell interactions.

Example 13

VAP-1 and mouse CyCAP share mimotypic identity

Provided below are experiments showing that the 90 kD mAb 1B2-immunoprecipitate is composed of human VAP-1 and of a cross-reactive mouse CyCAP.

Materials and Methods

Cells and Tissues

COS-7 and Namalwa cells were from American Type Culture Collection. Resident Balb/c mouse macrophages were collected from peritoneal cavity.

Immunofluorescence staining

COS-7 cells grown on 8 well plastic slides (LabTek chamber slides, Nunc) and cytocentrifuge preparations of Namalwa cells were stained using a protocol described earlier (Salmi et al. *J. Cell. Biol.* 122:431–442 (1993)). Briefly, the cells were fixed in 1% formalin and permeabilized by acetone. Primary antibodies were added at 20 μg/ml (diluted in PBS containing 1% FCS and 1 mM sodium azide), and FITC-conjugated sheep anti-mouse Ig along with 5% human AB-serum was used as a second-stage reagent. Thereafter, cells were mounted in 50% glycerol, 2×PBS, 0.1% sodium azide and 100 μg/ml DABCO (1,4-diazabicyclo(2,2,2)octane, Sigma).

Mouse CyCAP and human Mac-2-BP transfectants

Total RNA was isolated from Balb/c resident peritoneal macrophages using acid guanidium thiocyanate-phenol-chloroform extraction. Using oligo dT primer and MMLV reverse transcriptase aliquots of this RNA were reverse transcribed into cDNA (Sambrook et at., *Molecular Cloning: A Laboratory Manual,* Cold Spring Harbor Press, Cold Spring Harbor, N.Y. (1989)). A full-length mCyCAP cDNA was amplified by PCR using two specific primers designed on the basis of the published mCyCAP sequence (5' CTIG-GATCCAGGCAATGGCTCTCCTGT 3' [SEQ.ID.NO.3] and 5'CCCCTCGAGTYACACCATGTCAGTGGAGT 3' [SEQ.ID.NO.4]) using standard reaction conditions and 1 min at 94° C., 1 min at 57° C. and 2 min at 72° C. for 35 cycles in a Perkin Elmer Cetus DNA Thermal Cycler. A PCR product of the expected size was isolated from agarose gel, digested with BamHI and XhoI and subcloned into expression vector pcDNA3 (Invitrogen Corp., San Diego Calif.) digested with the same restriction enzymes (Sambrook et al., *Molecular Cloning: A Laboratory Manual,* Cold Spring Harbor Press, Cold Spring Harbor, N.Y. (1989)). The sequence of the cloned 1.7 kb PCR fragment was verified by sequencing and found to be identical with the published mCyCAP sequence. Twenty micrograms mCyCAP cDNA containing pcDNA3 plasmid or pcDNA3 plasmid alone were transfected into COS-7 (0.3 kV, 960 µF) and Namalwa (0.45 kV, 960/µF) cells by electroporation (BioRad Gene Pulser Apparatus). Cells were grown in RPMI 1640 supplemented with 10% FCS, penicillin and streptomycin, and stable transfectants were generated from Namalwa cells by continuous selection with geneticin (1.5 mg/ml).

Mac-2-BP clones were found from screening of a tonsil cDNA library made in bacterial expression vector λgt22A with a pool of six 59 mer degenerate oligonucleotides designed on the basis of the previously obtained N-terminal amino acid sequence of the 90 kD 1B2-immunopurified material using standard techniques (Sambrook et al., *Molecular Cloning: A Laboratory Manual,* Cold Spring Harbor Press, Cold Spring Harbor, N.Y. (1989)). After confirming that the whole insert sequence was identical with the published Mac-2-BP sequence, the insert was subcloned into pCDNA3 mammalian expression vector and used for electroporation of COS-7 and Namalwa cells.

Results

In an attempt to clone the cDNA encoding the 90 kD molecule we used a degenerate pool of 59 mer oligonucleotides designed on the basis of its N-terminal sequence to screen a human tonsil λgt22A library. Several cDNA clones were isolated that proved to be identical with human Mac-2 binding protein (Mac-2-BP, Koths et al., *J. Biol. Chem.* 268:14245–14249 (1993)). No other cDNAs with higher similarity to the peptide were isolated. During the course of these experiments, a mouse cyclophilin C associated protein (mCyCAP) cDNA sequence was published (Friedman et al., *Proc. Natl. Acad. Sci. USA* 90:6815–6819 (1993)) that predicted a protein with 100% identity to the N-terminal sequence of the 90 kD 1B2 reactive molecule previously reported (Salmi et al., *Science* 257:1407–1409 (1992)). mCyCAP also has 67% identity to Mac-2-BP. Therefore, we next considered the possibility that the 90 kD 1B2-immunoreactive species obtained in affinity-purification might consist of two proteins: a human molecule (as revealed by metabolic labeling of human tonsil) and a co-precipitating mCyCAP. Clearly, the mouse protein would have to bind to mAb 1B2 during the production of the mAb in NS-1 cells, since no material of mouse origin was present during later purification stages. We first confirmed the expression of mCyCAP in NS-1 hybridoma cells by showing the presence of mCyCAP mRNA in these cells by reverse transcriptase PCR (data not shown). Thereafter, we set up an experiment where two identical CnBr-activated SEPHAROSE™-4B (beaded agarose) columns coupled with mAb 1B2 were used: to one human tonsil lysate was applied and to the other no lysate was added (=empty column). After elution with triethylamine, samples from both columns were separated in SDS-PAGE and the proteins visualized by silver staining. The prominent 90 kD band was observed both from the lysate containing (FIG. 14A) and from the empty 1B2 column (FIG. 17, lane 1). Moreover, the 90 kD proteins from both columns had the same N-terminal sequence. Thus, mCyCAP can bind to mAb 1B2. However, this binding is a highly specific event, since mCyCAP does not associate with several other mAbs analogously coupled to SEPHAROSE™ (beaded agarose) (FIG. 17, lanes 2–3). All mAbs used in these binding experiments have been produced in NS-1 hybridomas and been cultured and purified under identical conditions. Moreover, mCyCAP only associates with a minor population of mAb 1B2 since in a silver stained gels only the native 150 kD mAb molecule is detectable, when 5 µg mAb is loaded. However, when milligram quantities (3000 times more) of 1B2 mAb (3 mg/ml beads, 5 ml columns) is covalently linked to CnBr-activated SEPHAROSE™-4B (beaded agarose) beads the absolute amount of co-immobilized mCyCAP that is recovered after elution becomes significant.

Intriguingly, mAb 5B11 that was raised against a synthetic peptide of the mCyCAP N-terminal sequence (before we knew of its origin) stained human tissues in similar manner to 1B2, detected a human 170 kD molecule in immunoblotting, and inhibited human PBL binding to venules in human tonsil (see Example 12 above). Therefore, we wanted to know, whether mAb 5B11 also recognizes mCyCAP. To that end, a full-length mCyCAP cDNA was produced by RT-PCR on total mouse macrophage RNA, subcloned into the eukaryotic expression vector pCDNA3, and transfected into COS-7 and Namalwa cells by electroporation. After transient expression in COS-7, cells were fixed, permeabilized and stained for immunofluorescence with mAbs 5B 11, 1B2, and 3B 11. However, none of these antibodies showed any staining. Similar results were obtained with stable transfected Namalwa cells (data not shown). Hence, protein folding rather than primary sequence is decisive in producing the 5B 11 epitope.

Since mCyCAP and human Mac-2-BP belong to the same superfamily of proteins containing a scavenger receptor cysteine rich (SRCR) domain (Freeman et al., *Proc. Natl. Acad. Sci. USA* 87:8810–8814 (1990)), and are 67% identical in overall amino acid sequence, we wanted to rule out identity between Mac-2-BP and the 90 kD form of VAP-1. Mac-2-BP transfectants were produced by subcloning a full-length Mac-2-BP clone obtained from the tonsil λgt22A cDNA library into the expression vector pCDNA3, and transfecting COS-7 and Namalwa cells with the construct. When these cells were stained for intracellular antigens, a clear granular cytoplasmic staining was observed with a known anti-Mac-2-BP antibody SP2. In contrast, mAbs 1B2, 5B11, and 3B 11 completely lacked reactivity with both transfectants (data not shown). Moreover, staining of serial tonsil sections with mAbs 1B2 and SP2 revealed clearly distinct reactivity profiles. Together, these results show that VAP-1 and Mac-2-BP are not identical proteins.

Discussion

The identity of the 90 kD protein that is specifically immunoprecipitated with mAb 1B2 was elucidated by showing that it comprised of two molecules: 1) a human tonsil protein (the 90 kD form of VAP-1) and 2) a cross-reactive mCyCAP. The human 90 kD form of VAP-1 was detected by metabolic labeling in a tonsil organ culture model and in surface-iodination of tonsil tissue fragments. This species of VAP-1 also appears to be sialylated, since its molecular mass is reduced after neuraminidase-treatment. The 90 kD form was not seen in immunoblotting or in the HEC line. Thus, it can represent a proteolytic degradation product of the larger molecule that loses the mAb 1B2 epitope. It is also possible that the 90 kD molecule would be a co-precipitating molecule firmly attached to 170 kD VAP-1 antigen during the purification process, but which would then dissociate during the electrophoresis. In this case the 90 kD human molecule could be the lymphocyte ligand of VAP-1, since it was only observed in the metabolically labeled slices of tonsil tissue, which contain huge numbers of lymphocytes.

The majority of the 1B2 immunoprecipitable 90 kD material obtained from large-scale purifications was shown to be mCyCAP by several criteria. First, we found that the N-terminal sequence determined from the 90 kD protein is 100% identical with a predicted protein sequence of mCy-CAP (Friedman et al., *Proc. Natl. Acad. Sci. USA* 90:6815–6819 (1993)). Also, several internal sequences (spanning altogether more than 100 amino acids) from tryptic fragments of the 90 kD 1B2 immunoprecipitable molecule were 100% identical with mCyCAP. Secondly, the 90 kD band was recovered from 1B2-loaded SEPHAROSE™ (beaded agarose) beads to which no lysate had been added. Finally, this material from empty 1B2 beads gave the same N-terminal sequence as we had obtained earlier. However, binding of mCyCAP to mAb 1B2 was highly specific, since none of the control columns to which several different mAbs (all produced in NS-1 cells under identical conditions) were coupled yielded a 90 kD band after elution. mCyCAP bound to mAb 1B2 in an antigen-like manner, since it remained associated to mAb 1B2 during the SEPHAROSE™ (beaded agarose) bead blocking with washes of alternating pH 4-ph 8 cycles, and during the washing of beads with the lysis buffer, but eluted with triethylamine.

Figure 18:
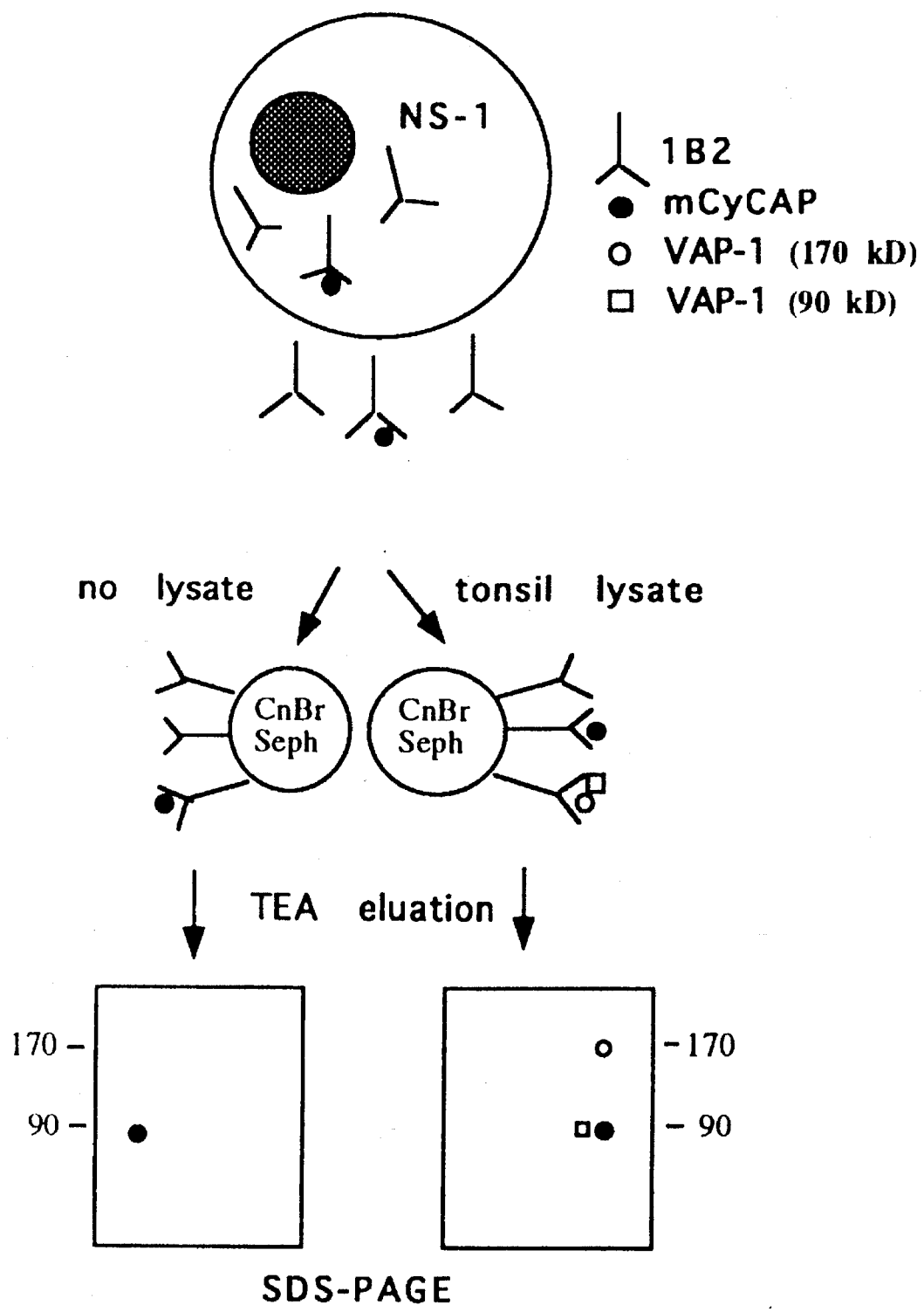
FIG. 18. Proposed mechanism for mCyCAP co-purification in large-scale mAb 1B2 affinity chromatography. A subpopulation of mAb 1B2 molecules binds mCyCAP when the antibody is being synthesized in NS-1 hybridomas. When large amount of mAb 1B2 is coupled to SEPHAROSE™ (beaded agarose) beads, substantial quantities of mCyCAP becomes simultaneously immobilized to the beads. Unoccupied mAb molecules can still bind VAP-1 from human tonsil lysates. After elution both mouse CyCAP and the human VAP-1 are recovered.

The only stage of the purification during which mCyCAP can bind to mAb 1B2 is the mAb synthesis in hybridomas. When milligram quantities of 1B2 are bound to the columns, the amount of co-immobilized mCyCAP becomes significant. Then by eluting the beads, more mCyCAP than the relatively rare human VAP-1 antigen bound from tonsil lysates is recovered (FIG. 18). The properties of mAb 5B11 that was generated against an N-terminal peptide from the 90 kD mCyCAP indicate that similarity between the 170 kD VAP-1 and mCyCAP must exist. mCyCAP, a member of the superfamily defined by the SRCR-domain (Freeman et al., *Proc. Natl. Acad. Sci. USA* 87:8810–8814 (1990)), is a glycoprotein that binds with high affinity to cyclophilin C, but to which no physiological function has yet been ascribed (Friedman et al., *Proc. Natl. Acad. Sci. USA* 90:6815–6819 (1993)). Thus, the 170 kD form of VAP-1 may also contain an SRCR domain. MAb 5B11 recognizes the N-terminal mCyCAP peptide in dot blot assays, but not in peptide EIA, and it does not react with mCyCAP transfectants or with the 90 kD band in immunoblotting of the 1B2-produced material. These data indicate that mCyCAP primary amino acid sequence is not sufficient to produce the 5B 11 epitope. Instead, subtle differences in peptide conformation, which occur during binding of peptides onto polystyrene in EIA plates versus nitrocellulose surfaces in dot blot assays, may be decisive in correct folding of the 5B11 epitope. In fact, mimotopes are examples of how primary sequence homology of two proteins is not necessary for mAb cross-reactivity. Mimotopes are defined as conformationally, but not linearly, related structures that react with a given antibody. For example, a functional anti-acetylcholine receptor mAb specifically recognizes a certain hexamer sequence from a peptide display phage library, although this sequence does not exist in the acetylcholine receptor (Balass et al., *Proc. Natl. Acad. USA* 90:10638–10642 (1993)). So far mimotopes have only been defined in nonproteinaceous molecules, and in the aforementioned case in the peptide display system. Thus, to our knowledge, our present findings are the first evidence that similar mechanisms may be operative during conventional mAb production in mouse. Taken together, our 5B11 data indicate that this particular mAb detects a protein epitope on a properly folded form of VAP-1. Since mAb 5B11 that blocks lymphocyte binding to vessels is against the SRCR-like domain of mCyCAP, a conformationally similar structure may be utilized in VAP-1 mediated adhesion to endothelial cells. Mimotypic identity of VAP-1 and mCyCAP N-terminus also explains why mCyCAP is specifically bound by mAb 1B2. Clearly, mAb 1B2 has to bind to mCyCAP in some late but transient maturational stage, since mCyCAP bound to mAb 1B2 has its signal peptide cleaved off, and it is glycosylated, and yet mAb 1B2 does not stain mouse cells and tissues.

Mac-2-BP (Koths et al., *J. Biol. Chem.* 268:14245–14249 (1993)) belongs to the same superfamily of molecules as mCyCAP and they are 67% identical in amino acid sequence. Mac-2-BP is a 90 kD galactose-specific S-type lectin binding glycoprotein expressed in macrophages and epithelial cells (Koths et al., *J. Biol. Chem.* 268:14245–14249 (1993); Cherayil et al., *Proc. Natl. Acad. Sci. USA* 87:7324–7328 (1990); Iacobelli et al., *FEBS* 319:59–65 (1993); Linsley et al., *Biochemistry* 25:2978–2986 (1986); Natali et al., *Cancer Res.* 42:583–589 (1982)). VAP-1 and Mac-2-BP are clearly distinct molecules, since their expression, molecular weights and functions are remarkably different. Moreover, none of our anti-VAP-1 mAbs reacted with two different transfectants that expressed Mac-2-BP.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosure of all references, patent applications, and patents cited herein are hereby incorporated by reference.

---

What is claimed is:

1. A method for detecting VAP-1 in bodily fluid from a patient, wherein said VAP-1 specifically binds monoclonal antibody 1B2 (DSM ACC2041), comprising:
   (1) removing a sample of the bodily fluid from the patient;
   (2) exposing said sample to a VAP-1-specific antibody; and
   (3) detecting VAP-1-specific antibody binding to VAP-1 present in said sample.

2. The method claim 1, where said sample is obtained from a source selected from the group consisting of plasma, serum and synovial fluid.

3. The method of claim 1, wherein said VAP-1-specific antibody is a polyclonal antibody.

4. The method of claim 1, wherein said VAP-1-specific antibody is a monoclonal antibody.

5. The method of claim 4, wherein said monoclonal antibody is 1B2 (DSM ACC2041).

6. The method of claim 1, wherein said VAP-1-specific antibody is raised against an immunogen selected from the group consisting of synovial stroma, the 170 kD form of VAP-1 wherein said 170 kD VAP-1 specifically binds monoclonal antibody 1B2 (DSM ACC2041), the 90 kD form of VAP-1 wherein said 90 kD VAP-1 specifically binds the monoclonal antibody 1B2 (DSM ACC2041) and a mimotope of VAP-1.

7. The method of claim 6, wherein said antibody is raised against a mimotope of VAP-1 derived from N-terminus of the mouse cyclophilin C associated protein.

8. The method of claim 7, wherein said N-terminus has the amino acid sequence LVNGASANEG.

9. The method of claim 8, wherein said VAP-1-specific antibody is monoclonal antibody 5B11 (DSM ACC2237).

10. A method for diagnosing a medical condition in a patient that is mediated by VAP-1-mediated binding of endothelial cells to lymphocytes, wherein said VAP-1 specifically binds monoclonal antibody 1B2 (DSM ACC2041), said method comprising:
   (1) removing cells from said patient suspected of being VAP-1 positive cells;

(2) exposing said cells of step (1) to a VAP-1-specific antibody;

(3) detecting VAP-1-specific antibody binding to said VAP-1 positive cells; and (4) diagnosing said medical condition on the basis of the amount of said binding.

11. The method of claim 10, wherein said VAP-1-specific antibody is a polyclonal antibody.

12. The method of claim 10, wherein said VAP-1-specific antibody is a monoclonal antibody.

13. The method of claim 12, wherein said monoclonal antibody is 1B2 (DSM ACC2041).

14. The method of claim 10, wherein said VAP-1-specific antibody is raised against an immunogen selected from the group consisting of synovial stroma, the 170 kD form of VAP-1 wherein said 170 Kd VAP-1 specifically binds monoclonal antibody 1B2 (DSM ACC2041), the 90 kD form of VAP-1 wherein said 90 kD VAP-1 specifically binds monoclonal antibody 1B2 (DSM ACC2041) and a mimotope of VAP-1.

15. The method of claim 14, wherein said antibody is raised against a mimotope of VAP-1 derived from the N-terminus of the mouse cyclophilin C associated protein.

16. The method of claim 15, wherein said N-terminus has the amino acid sequence LVNGASANEG.

17. The method of claim 16, wherein said VAP-1-specific antibody is monoclonal antibody 5B11 (DSM ACC2237).

18. The method of claim 10, wherein said medical condition is a chronic or acute infectious or inflammatory disease selected from the group consisting of arthritis, dermatosis, inflammatory bowel disease and autoimmune disease.

19. The method of claim 18, wherein said medical condition is rheumatoid arthritis.

20. The method of claim 18, wherein said medical condition is an inflammatory bowel disease selected from the group consisting of Crohn's disease and ulcerative colitis.

21. The method of claim 18, wherein said medical condition is a dermatosis selected from the group consisting of psoriasis, atopic eczema and lichen ruber planus.

* * * * *

UNITED STATES PATENT AND TRADEMARK OFFICE
CERTIFICATE OF CORRECTION

PATENT NO. : 5,512,442
DATED : April 30, 1996
INVENTOR(S) : Sirpa Jalkanen, et al.

It is certified that error appears in the above-indentified patent and that said Letters Patent is hereby corrected as shown below:

Column 36, line 61, claim 10 should read:

10. A method for aiding in diagnosing a medical condition in a patient who is undergoing inflammation by detecting VAP-1, wherein said VAP-1 specifically binds monoclonal antibody 1B2 (DSM ACC2041), said method comprising:
  (1) removing cells suspected of being VAP-1 positive cells from said patient;
  (2) exposing said cells of step (1) to VAP-1-specific antibody;
  (3) detecting VAP-1-specific antibody binding to said VAP-1 positive cells;
  (4) diagnosing said medical condition on the basis of increased binding of said binding compared to normal or noninflammed specimens.

Signed and Sealed this

Tenth Day of September, 1996

*Attest:*

BRUCE LEHMAN

*Attesting Officer*     *Commissioner of Patents and Trademarks*